US011279692B2

(12) United States Patent
Guggenheim et al.

(10) Patent No.: US 11,279,692 B2
(45) Date of Patent: Mar. 22, 2022

(54) METHODS FOR THE MANUFACTURE OF AN AROMATIC BISIMIDE AND A POLYETHERIMIDE

(71) Applicant: SABIC GLOBAL TECHNOLOGIES B.V., Bergen op Zoom (NL)

(72) Inventors: Thomas Link Guggenheim, Mount Vernon, IN (US); Roy Ray Odle, Mount Vernon, IN (US); Mani Raj Chaulagain, Mount Vernon, IN (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 546 days.

(21) Appl. No.: 16/065,246

(22) PCT Filed: Dec. 29, 2016

(86) PCT No.: PCT/US2016/069309
§ 371 (c)(1),
(2) Date: Jun. 22, 2018

(87) PCT Pub. No.: WO2017/117449
PCT Pub. Date: Jul. 6, 2017

(65) Prior Publication Data
US 2021/0206747 A1   Jul. 8, 2021

Related U.S. Application Data

(60) Provisional application No. 62/272,480, filed on Dec. 29, 2015.

(51) Int. Cl.
*C07D 403/12*     (2006.01)
*C07D 209/48*     (2006.01)
*C08G 73/10*      (2006.01)

(52) U.S. Cl.
CPC ......... *C07D 403/12* (2013.01); *C07D 209/48* (2013.01); *C08G 73/1046* (2013.01)

(58) Field of Classification Search
CPC .. C07D 403/12; C07D 209/48; C07D 209/34; C08G 73/1046
See application file for complete search history.

(56) References Cited

U.S. PATENT DOCUMENTS

| | | | | |
|---|---|---|---|---|
| 3,847,867 A | * | 11/1974 | Heath et al. | C08G 73/1053 528/26 |
| 3,847,870 A | | 11/1974 | Takekoshi | |
| 3,855,178 A | | 12/1974 | White et al. | |
| 3,868,389 A | * | 2/1975 | Takekoshi | C07D 209/48 548/462 |
| 3,879,428 A | * | 4/1975 | Heath | C07D 209/48 549/241 |
| 3,923,828 A | | 12/1975 | Williams | |
| 3,933,852 A | * | 1/1976 | Cook | C07D 209/48 548/480 |
| 4,005,102 A | * | 1/1977 | Cook | C07B 43/02 548/481 |
| 4,017,511 A | * | 4/1977 | Williams, III | C07D 209/48 548/461 |
| 4,054,577 A | * | 10/1977 | Relles | C07D 209/48 548/461 |
| 4,599,429 A | * | 7/1986 | Odle | C07D 209/48 548/473 |
| 4,681,949 A | * | 7/1987 | Brunelle | C07D 209/48 544/280 |
| 4,902,809 A | * | 2/1990 | Groeneweg | C07D 209/48 548/481 |
| 4,988,544 A | * | 1/1991 | Cella | C08G 73/101 427/384 |
| 5,081,298 A | * | 1/1992 | Brunelle | C07C 205/38 502/167 |
| 5,116,975 A | * | 5/1992 | Brunelle | C07C 205/38 544/129 |

(Continued)

FOREIGN PATENT DOCUMENTS

| | | | |
|---|---|---|---|
| CA | 2034435 A1 | * | 8/1991 |
| CA | 2044470 A1 | * | 9/1992 |

(Continued)

OTHER PUBLICATIONS

N.G. Anderson, Practical Process & Research Development (2000) (Year: 2000).*
CAS/CASREACT Abstract and Indexed Reaction, D. Brunelle et al., CA 2034435 (1991) (Year: 1991).*
Feng, Ya-qing et al., "Synthesis of new carbamic acid ethyl esters", Tianjin Daxue Xuebao, Journal vol. 37, Issue 5, 2004; pp. 447-450. English abstract only, 1 page.
Kuang, Yongqing et al., "Synthesis of 6-[(N-(4-aminobutyl)-N-ethyl]amino-2,3-dihydro-1,4-phthalazinedione", Disi Junyi Daxue Xuebao, Journal vol. 23, Issue 11, 2002; pp. 1037-1039. English abstract only, 1 page.
Kuang, Yongqing et al., "Synthesis of N-methyl-4-aminophthalimide", Huaxue Shiji, Journal vol. 14, Issue 5, 1992; pp. 315, 301. English abstract only, 1 page.
Matveev, V. A. et al., "Synthesis of N-substituted imides of halo- and nitrophthalic acids", Izvestiya Akademii Nauk Kazakhskoi SSR, Seriya Khimicheskaya, Journal vol. 1, 1991; pp. 54-57. English abstract only, 1 page.

(Continued)

*Primary Examiner* — Alexander R Pagano
(74) *Attorney, Agent, or Firm* — Cantor Colburn LLP

(57) ABSTRACT

A method for producing an aromatic bisimide includes reacting a dialkali metal salt of a dihydroxy aromatic compound with an N-alkyl nitrophthalimide to form a product mixture including the aromatic bisimide. The N-alkyl nitrophthalimide includes 4-nitro-N—($C_{1-13}$ alkyl)phthalimide, 3-nitro-N—($C_{1-13}$ alkyl)phthalimide, or a combination including at least one of the foregoing, and 4-hydroxy-3,5-dinitro-N—($C_{1-13}$ alkyl)phthalimide in an amount of 1-10000 ppm. The aromatic bisimide can be obtained in a yield of greater than 75%, or 90-99.8%. A method for the manufacture of a polyetherimide, a polyetherimide, and an article including the polyetherimide are also disclosed. A mixed acid nitration process for the preparation of an N-alkyl nitrophthalimide is also described.

13 Claims, No Drawings

(56) References Cited

U.S. PATENT DOCUMENTS

| | | | | |
|---|---|---|---|---|
| 5,208,346 | A | * | 5/1993 | Dellacoletta .......... C07D 209/48 548/461 |
| 5,536,846 | A | * | 7/1996 | Dellacoletta .......... C07D 209/48 549/252 |
| 5,756,843 | A | | 5/1998 | Webb et al. |
| 5,969,086 | A | * | 10/1999 | Webb .................... B01J 31/0239 528/271 |
| 6,008,374 | A | * | 12/1999 | Dellacoletta .......... C07D 307/89 548/461 |
| 6,251,354 | B1 | * | 6/2001 | Greenwell .............. C01B 21/50 423/385 |
| 7,759,468 | B1 | | 7/2010 | Hicks et al. |
| 8,080,671 | B2 | * | 12/2011 | Guggenheim ........ C07D 209/48 548/473 |
| 2004/0063897 | A1 | * | 4/2004 | Odle ..................... C07D 209/48 528/170 |
| 2007/0073063 | A1 | * | 3/2007 | Stella .................... C07D 209/48 548/461 |
| 2008/0085890 | A1 | | 4/2008 | Tsou et al. |
| 2012/0029125 | A1 | * | 2/2012 | Gallucci ................. C08L 79/08 524/153 |
| 2014/0099510 | A1 | * | 4/2014 | Chiong ................. C08G 65/485 428/473.5 |
| 2018/0044474 | A1 | * | 2/2018 | Guggenheim ..... C08G 73/1046 |
| 2019/0092726 | A1 | * | 3/2019 | Schulte, II ............. C09K 21/14 |
| 2019/0135750 | A1 | * | 5/2019 | Croll .................. B01D 11/0492 |

FOREIGN PATENT DOCUMENTS

| | | |
|---|---|---|
| EP | 0147798 A2 | 7/1985 |
| EP | 0184595 A1 | 6/1986 |
| GB | 1510735 | 5/1978 |
| KR | 1020080091551 A | 10/2008 |
| RU | 2044726 C1 | 9/1995 |
| SU | 1740373 A1 | 6/1992 |

OTHER PUBLICATIONS

Zhang, Fan et al., "Reagent for chemiluminescent immunoassay—a new synthetic route for 6-[N-(4-aminobutyl)-N-ethyl]amino-2,3-dihydro-1,4-phthalazinedione", Huaxue Shiji, Journal vol. 14, Issue 4, 1992; pp. 207-208. English abstract only, 1 page.

Zhang, Ya-nan et al., "Study on synthesis of N-methyl-4-aminophthalimide", Guangzhou Huagong, Journal vol. 37, issue 8, 2009; pp. 111-112, 115. English abstract only, 1 page.

Zheng, Kai et al., "New synthesis method of 4-nitro-N-methylphthalimide", Shiyou Huagong, Journal vol. 33, Issue 2, 2004; pp. 145-148. English abstract only, 1 page.

Zheng, Kai et al., "New synthetic method for 4-nitro-N-methylphthalimide", Jiangsu Huagong, Journal vol. 31, Issue 6, 2003; pp. 39-41. English abstract only, 1 page.

Amarjit Luniwal et al., "Molecular docking and enzymatic evaluation to identify selective inhibitors of aspartate semialdehyde dehydrogenase" Bioorganic & Medicinal Chemistry, vol. 20, 2012, pp. 2950-2956.

Frank J. Williams et al., "Nitration of N-Alkylphthalimides", American Chemical Society, Journal of Organic Chemistry, vol. 43, No. 8, 1798, pp. 1608-1610.

Hajime Karatani, "Microenvironmental Effects of Water-Soluble Polymers on the Chemiluminescence of Luminol and Its Analogs" The Chemical Society of Japan, vol. 60, Jun. 1987, pp. 2023-2029.

International Search Report issued in Application No. PCT/US2016/069309 dated Feb. 22, 2017.

Joonseok Koh et al., "Synthesis and Spectral Properties of Phthalimide Based Alkali-clearable Azo Disperse Dyes", Fibers and Polymers, vol. 9, No. 2, 2008, pp. 143-151.

Sheng-Yin Zhao et al., "N-Methylation of NH-Containing Heterocycles with Dimethyl Carbonate Catalyzed by TMEDA" Syntheic Communications, An International Journal for Rapid Communication of Synthetic Organic Chemistry, vol. 42, 2012, pp. 128-135.

Sundar Neelakantan et al., "Synthesis of novel isoluminol probes and their use in rapid bacterial assays" Bioorgnaic & Medicinal Chemistry Letters, vol. 19, 2009, pp. 5722-5726.

Vittorio Pace et al., "2-Methyltetrahydrofuran as a suitable green solvent for phthalimide functionalization promoted by supported KF", The Royal Society of Chemistry, Green Chemistry, vol. 12, 2010, pp. 1380-1382.

Written Opinion issued in Application No. PCT/US2016/069309 dated Feb. 22, 2017.

Xiaoli Bian et al., "A new series of N2-substituted-5-(p-toluenesulfonylamino)phthalimide analogues as a-glucosidase inhibitors" Bioorganic & Medicinal Chemistry Letters, vol. 23, 2013, pp. 2022-2026.

Xin-Hong Duan et al., "Novel anilinophthalimide derivaties as potential probes for b-amyloid plaque in the brain", Bioorganic & Medicinal Chemistry, vol. 18, 2010, pp. 1337-1343.

* cited by examiner

METHODS FOR THE MANUFACTURE OF AN AROMATIC BISIMIDE AND A POLYETHERIMIDE

CROSS-REFERENCE TO RELATED APPLICATIONS

This application is a National Stage application of PCT/US2016/069309, filed Dec. 29, 2016, which claims the benefit of U.S. Provisional Application No. 62/272,480, filed Dec. 29, 2015, both of which are incorporated by reference herein in their entirety.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare the articles.

N-substituted nitrophthalimides are useful starting reactants for making a variety of organic dianhydrides, bisimides, and polyimides. One method for preparing N-substituted nitrophthalimides is by reacting nitrophthalic anhydride and an organic isocyanate in the presence of an alkali carbonate catalyst. See, e.g., U.S. Pat. No. 3,868,389. In another method, a solution of N-alkylphthalimide in a solvent comprising 98-103 wt % concentrated sulfuric acid is contacted with 98-100 wt % concentrated nitric acid within a temperature range of 35-80° C., then the reaction product is isolated by methylene chloride extraction. See, e.g., U.S. Pat. No. 3,933,852. Another method is a nitric acid-only process. See, e.g., U.S. Pat. No. 4,902,809.

In addition to the 3- and 4-isomers of N-alkyl nitrophthalimide produced by the above-described processes, a minor amount of di-nitro derivatives of the N-alkyl phthalimide can also be formed, particularly when a combination of nitric acid and sulfuric acid is used. The primary di-nitro derivative formed is 3,5-di-nitro-4-hydroxy-N-alkyl phthalimide (DNPI). The presence of such di-nitro derivatives has generally been regarded as undesirable due to the detrimental effect on subsequent nitro displacement reactions, namely the formation of the desired bisimides in poor yields or the formation of high color bisimides which when converted to polymer, can lead to polymer discoloration. Accordingly, there has been intensive research and development directed to the removal of the di-nitro derivatives formed by various nitration process.

It would be advantageous to provide a method for manufacturing an aromatic bisimide in the presence of a di-nitro byproduct, where the aromatic bisimide can be provided in high yield, and preferably have low color. Accordingly, there is a continuing need for improved methods of manufacturing aromatic bisimides and the corresponding polyetherimides.

BRIEF DESCRIPTION

A method for producing an aromatic bisimide comprises reacting a dialkali metal salt of a dihydroxy aromatic compound with an N-alkyl nitrophthalimide composition under conditions effective to form a product mixture comprising the aromatic bisimide, wherein the N-alkyl nitrophthalimide composition comprises 4-nitro-N—($C_{1-13}$ alkyl)phthalimide, 3-nitro-N—($C_{1-13}$ alkyl)phthalimide, or a combination comprising at least one of the foregoing, and 4-hydroxy-3,5-dinitro-N—($C_{1-13}$ alkyl)phthalimide in an amount of 1-10000 ppm, or 50-10000 ppm, or 100-10000 ppm, or 500-10000 ppm, or 1000-10000 ppm; 1-8000 ppm, or 50-8000 ppm, or 100-8000 ppm, or 500-8000 ppm, or 1000-8000 ppm or 1-8000 ppm, or 50-8000 ppm, or 100-7000 ppm, or 500-7000 ppm, or 1000-7000 ppm; or 1-6000 ppm, or 50-6000 ppm, or 100-6000 ppm, or 500-6000 ppm, or 1000-6000 ppm; or 1-4000 ppm, or 50-4000 ppm, or 100-4000 ppm, or 500-4000 ppm, or 1000-4000 ppm; or 1-3000 ppm, or 50-3000 ppm, or 100-3000 ppm, or 500-6500, or 500-3000 ppm, or 1000-3000 ppm; and wherein the aromatic bisimide is obtained in a yield of greater than 75%, or greater than 85%, or 90-99.8%, or 95-99.8%, or 97-99.8%, or 98-99.8%, or 99-99.8%.

A method for the manufacture of a polyetherimide comprises contacting an aromatic bisimide prepared by the above method with a phthalic anhydride in the presence of a catalyst and under conditions effective to provide an aromatic bis(ether phthalic anhydride) of the formula

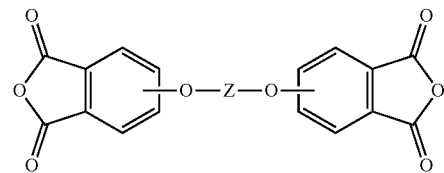

wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of the formula $H_2N$—R—$NH_2$ wherein R is a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof, or a combination comprising at least one of the foregoing; and wherein the polyetherimide has a YI of less than 120, or less than 110, or less than 100, as determined according to ASTM D1925 at a thickness of 3.2 millimeters.

Another method for the manufacture of a polyetherimide comprises hydrolyzing an aromatic bisimide prepared by the above method under conditions effective to provide the corresponding tetraacid; and condensing the tetraacid under conditions effective to provide an aromatic bis(ether phthalic anhydride) of the formula

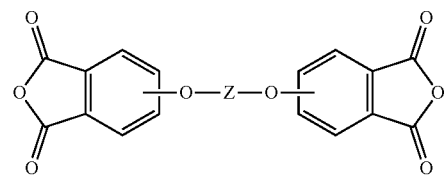

wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of the formula $H_2N$—

R—NH$_2$ wherein R is a C$_{6-20}$ aromatic hydrocarbon group or a halogenated derivative thereof, a straight or branched chain C$_{2-20}$ alkylene group or a halogenated derivative thereof, a C$_{3-8}$ cycloalkylene group or halogenated derivative thereof, or a combination comprising at least one of the foregoing; and wherein the polyetherimide has a YI of less than 120, or less than 110, or less than 100, as determined according to ASTM D1925 at a thickness of 3.2 millimeters.

A polyetherimide prepared according to the above method and an article comprising the polyetherimide are also disclosed.

A mixed acid nitration process for the preparation of an N-alkyl nitrophthalimide composition, the process comprising contacting an N-alkylphthalimide with nitric acid and sulfuric acid, to provide a dissolved N-alkyl nitrophthalimide product mixture comprising 4-nitro-N—(C$_{1-13}$ alkyl) phthalimide, 3-nitro-N—(C$_{1-13}$ alkyl)phthalimide, or a combination comprising at least one of the foregoing, and 4-hydroxy-3,5-dinitro-N—(C$_{1-13}$ alkyl)phthalimide; adding water to precipitate the N-alkyl nitrophthalimide product mixture, and isolating the precipitated N-alkyl nitrophthalimide product mixture; washing the isolated N-alkyl nitrophthalimide product mixture, preferably wherein the washing is using a belt filter, an agitated nutsche filter, centrifuging, or a combination comprising at least one of the foregoing, to provide a washed N-alkyl nitrophthalimide composition; and optionally purifying the washed N-alkyl nitrophthalimide product mixture by: contacting the washed N-alkyl nitrophthalimide product mixture with an aqueous alkali metal carbonate solution, an aqueous alkali metal hydrogen carbonate solution, or a combination comprising at least one of the foregoing, followed by extracting the 4-nitro-N—(C$_{1-13}$ alkyl)phthalimide into an organic solvent provide an aqueous phase and an organic phase; and separating aqueous phase and the organic phase to provide a purified N-alkyl nitrophthalimide composition in the organic phase; or dissolving the washed N-alkyl nitrophthalimide product mixture in an organic solvent immiscible with water to extract the 4-nitro-N—(C$_{1-13}$ alkyl)phthalimide into the organic solvent and provide an aqueous phase and an organic phase; adding an aqueous alkali metal carbonate, an aqueous alkali metal hydrogen carbonate, or a combination thereof to the aqueous phase; and separating aqueous phase and the organic phase to provide a purified N-alkyl nitrophthalimide composition in the organic phase; or dissolving the washed N-alkyl nitrophthalimide product mixture in an organic solvent immiscible with water to extract the 4-nitro-N—(C$_{1-13}$ alkyl)phthalimide into the organic solvent and provide an aqueous phase and an organic phase; and separating aqueous phase and the organic phase to provide a purified N-alkyl nitrophthalimide composition in the organic phase; and optionally further contacting the organic phase with an aqueous alkali metal hydrogen carbonate solution, or a combination comprising at least one of the foregoing to provide an organic phase comprising a purified N-alkyl nitrophthalimide composition wherein the washed or the purified N-alkyl nitrophthalimide composition comprises 4-nitro-N—(C$_{1-13}$ alkyl)phthalimide, 1-10000 ppm, or 1-8000 ppm, or 1-7000 ppm, or 1-6000 ppm, or 1-5000 ppm, or 1-4000 ppm, or 1-3000 ppm, or 500-7000 ppm, 500-6000 ppm, or 500-5000 ppm, or 500-4000 ppm, or 500-3000 ppm, or 1000-7000 ppm or 1000-6000 ppm, or 1000-5000 ppm or 1000-4000 ppm, or 1000-3000 of 4-hydroxy-3,5-dinitro-N—(C$_{1-13}$ alkyl)phthalimide, and 0.001-5 wt %, or 0.1 to 3.5 wt. %, or 1-2 wt % of 3-nitro-N—(C$_{1-13}$ alkyl)phthalimide.

The above described and other features are exemplified by the following detailed description.

DETAILED DESCRIPTION

The present inventors have unexpectedly discovered that an aromatic bisimide suitable for the preparation of low color polymers can be prepared by the reaction of a dialkali metal salt of a dihydroxy aromatic compound with an N-alkyl nitrophthalimide composition in the presence of a di-nitro byproduct, in particular 4-hydroxy-3,5-dinitro-N—(C$_{1-13}$ alkyl)phthalimide. Advantageously, the aromatic bisimide obtained by the methods described herein can be isolated in high yields (e.g., greater than 75%) and can optionally have low color (e.g., a yellowness index (YI) of less than less than 25).

Accordingly, one aspect of the present disclosure is a method for producing an aromatic bisimide. The method comprises reacting a dialkali metal salt of a dihydroxy aromatic compound with an N-alkyl nitrophthalimide composition under conditions effective to form a product mixture comprising the aromatic bisimide.

The N-alkyl nitrophthalimide composition can be made by a variety of methods that produce the 4-hydroxy-3,5-dinitro-N—(C$_{1-13}$ alkyl)phthalimide side product. For example, in some embodiments, the N-alkyl nitrophthalimide composition can be prepared by contacting an N-alkyl phthalimide with nitric acid and sulfuric acid to provide a nitration product mixture comprising 3- and 4-nitro-N-alkyl phthalimide and 4-hydroxy-3,5-dinitro-N-alkyl phthalimide. The nitric acid and sulfuric acid and the N-alkyl phthalimide can be mixed together in a reactor, preferably a reactor equipped with a stirrer and means for heating or cooling the reactor. Alternatively, the N-alkyl phthalimide can be dissolved in the sulfuric acid, and the desired molar equivalents of nitric acid can be added to the solution at the desired rate and temperature. The reactor can be such as to allow for either batch or continuous processing. The N-alkyl phthalimide can be added to the reactor in any suitable form, e.g., powder, flake, etc., but is preferably in liquid form.

The N-alkyl phthalimide is an N—(C$_{1-13}$ alkyl)phthalimide, and the nitration product mixture comprises 4-nitro-N—(C$_{1-13}$ alkyl)phthalimide, or 4-nitro-N-methylphthalimide, and 4-hydroxy-3,5-dinitro-N—(C$_{1-13}$ alkyl)phthalimide, specifically 4-hydroxy-3,5-dinitro-N-methylphthalimide ("DNPI"). In some embodiments, the nitration product mixture can further include 3-nitro-N—(C$_{1-13}$ alkyl) phthalimide, or 3-nitro-N-(methyl)phthalimide. The 4-hydroxy-3,5-dinitro-N—(C$_{1-13}$ alkyl)phthalimide, specifically the DNPI, can be present in the product mixture in an amount of 1-10000 ppm, or 50-10000 ppm, or 100-10000 ppm, or 500-10000 ppm, or 1000-10000 ppm; 1-8000 ppm, or 50-8000 ppm, or 100-8000 ppm, or 500-8000 ppm, or 1000-8000 ppm or 1-8000 ppm, or 50-8000 ppm, or 100-7000 ppm, or 500-7000 ppm, or 1000-7000 ppm; or 1-6000 ppm, or 50-6000 ppm, or 100-6000 ppm, or 500-6000 ppm, or 1000-6000 ppm; or 1-4000 ppm, or 50-4000 ppm, or 100-4000 ppm, or 500-4000 ppm, or 1000-4000 ppm; or 1-3000 ppm, or 50-3000 ppm, or 100-3000 ppm, or 500-3000 ppm, or 1000-3000 ppm of the 4-hydroxy-3,5-dinitro-N—(C$_{1-13}$ alkyl)phthalimide, specifically DNPI.

The nitric acid and sulfuric acid are concentrated nitric acid and concentrated sulfuric acid. The concentrated nitric acid can be 60-100%, or 70-100%, or 80-100%, or 90-100%, or 95-100%, or 98-100%, or 60-70%, or 60-80%, or 60-90%, or 60-99% by weight concentrated nitric acid. In some embodiments, the concentrated nitric acid is 90-99%, or 99% by weight concentrated nitric acid.

The concentrated sulfuric acid can be 70-100%, or 80-100%, or 85-100%, or 90-100%, or 95-100%, or 98-100%, or 70-80%, or 70-85%, or 70-90%, or 70-95%, or 70-98% by weight concentrated sulfuric acid. In some embodiments, the concentrated sulfuric acid is 90-99% by weight concentrated sulfuric acid, or 98% by weight concentrated sulfuric acid. In some embodiments, the concentrated sulfuric acid can be greater than 100% concentrated sulfuric acid, e.g., by the addition of oleum, also known as fuming sulfuric acid. Thus, the concentrated sulfuric acid can be 70-105%, or 80-105%, or 85-105%, or 90-105%, or 95-105%, or 98-105%, or 95-103%, or 98-103%, or 99-103%, or 100-103% by weight concentrated sulfuric acid.

The contacting of the N-alkyl phthalimide with the nitric acid and sulfuric acid can be in any order, however for safety and process reasons, it is preferred that the N-alkyl phthalimide is first dissolved in concentrated sulfuric acid to achieve a 10-40 wt %, or 15-40 wt %, or 20-40 wt %, or 25-35 wt %, or 28-32 wt % solution of N-alkyl phthalimide in the sulfuric acid. Concentrated nitric acid can be slowly added to the sulfuric acid solution. The nitric acid can be added such that the N-alkyl phthalimide and the nitric acid are present in the mixed acid nitration product mixture in a molar ratio of 1:1 to 1:3, or 1:1 to 1:2, or 1:1 to 1:1.5, or 1:1.1 to 1:1.3. The addition of nitric acid constitutes an exothermic reaction, which is preferably controlled by cooling the reactor. Alternatively, in some embodiments, the nitric acid and the sulfuric acid can be premixed, and the combination can be contacted with the N-alkyl phthalimide. In some embodiments, the N-alkyl phthalimide, the nitric acid, and the sulfuric acid can be mixed simultaneously.

The mixed acid nitration can be carried out at a temperature of less than or equal to 60° C., for example 25-60° C., or 30-60° C., or 35-60° C., or 40-60° C., or 45-55° C. In an embodiment, the nitration is carried out at a temperature of 40-55° C., with the N-alkyl phthalimide and the nitric acid present in a molar ratio of less than 1:1.3, or 1:1.15 to 1:1.3. Temperatures outside the range of temperatures disclosed above also can be used; however, lower temperatures can result in a reaction rate that is too slow to be cost effective, and higher temperatures can require operation at above atmospheric pressure to prevent boiling and subsequent loss of nitric acid. In particular, temperatures greater than 60° C. and molar ratios of N-alkyl phthalimide to nitric acid greater than 1:1.3 are generally avoided for safety reasons. The percent solids in the mixed acid nitration can be 5-50%, 10-40%, 20-35%, 25-35%, 25-30% or 28-31%, by weight, based on the total weight of the nitration product mixture. In other embodiments, the percent solids in the mixed acid nitration can be 10-90%, or 40-90%, or 50-90%, or 20-80%, or 10-50%, or 20-50%, or 30-50%, or 40-50%, or 10-40%, or 10-30%, or 10-20%, or 20-40%, or 20-30%, or 30-40% by weight, based on the total weight of the nitration product mixture. In some embodiments, the percent solids in the nitration product mixture can be 25-35%.

The pressure range under which the nitration process operates can vary from vacuum to above atmospheric pressure. Such conditions, however, depend on the type of reactor or reactors employed. Otherwise, the process is generally run at atmospheric pressure.

The nitration reaction is preferably allowed to proceed until less than 5 weight percent (wt %), or less than 2 wt %, or less than 1 wt %, or less than 0.5 wt %, or less than 0.1 wt % of N-alkyl phthalimide remains in the nitration product mixture.

It is further possible to conduct the nitration reaction by an all-nitric acid process using the conditions found in U.S. Pat. No. 4,902,809. In this embodiment, 4-hydroxy-3,5-dinitro-N—($C_{13}$ alkyl)phthalimide, specifically DNPI, can be present in the nitration product mixture, particularly when the nitration reaction fails to progress to the point that less than 5 wt %, or less than 2 wt %, or less than 1 wt %, or less than 0.5 wt %, or less than 0.1 wt % of N-alkyl phthalimide remains unreacted in the nitration product mixture.

The particular conditions for reacting the dialkali metal salt of a dihydroxy aromatic compound with the N-alkyl nitrophthalimide composition to provide the aromatic bisimide will depend on the specific dihydroxy aromatic compounds, the specific components of the N-alkyl nitrophthalimide composition, the solvent, the presence of or absence of a phase transfer catalyst, and like considerations. For example, the reacting can be at a temperature of 25-250° C., for example, 100-250° C., or 115-200° C., or 100-125° C., or 115-125° C. The reacting can be at atmospheric pressure, superatmospheric pressure, or subatmospheric pressure. For example, the reacting can be at a pressure of 0-70 kPa, or 30-70 kPa, or 50-70 kPa, or 10-30 kPa, or 10-40 kPa, or 10-50 kPa, or 10-60 kPa, or 20-40 kPa, or 20-50 kPa, or 20-60 kPa, or 30-50 kPa, or 30-60 kPa, or 40-60 kPa.

The reaction mixture can have a solids content of 1-90 wt % (wt %), or 10-90 wt %, or 10-80 wt %, or 10-70 wt %, or 10-60 wt %, or 40-90 wt %, or 50-90 wt %, or 60-90 wt %, or 10-50 wt %, or 20-50 wt %, or 30-50 wt %, or 10-40 wt %, or 10-30 wt %, or 20-40 wt %, each based on the total weight of the reaction mixture, depending on the nature of the N-alkyl group. In some embodiments, the reaction mixture can have a solids content of 20-30 wt %, or 22-26 wt % based on the total weight of the reaction mixture. As used herein, "solids content" refers to the weight of the non-solvent components whether dissolved or in solid form divided by the total weight of the reaction mixture.

One mole equivalent of dialkali metal salt and 2 mole equivalents of N-alkyl nitrophthalimide composition can be used, while higher or lower amounts of either will not substantially interfere with the formation of the desired aromatic bisimide. In some embodiments, however, two moles of the N-alkyl nitrophthalimide composition per mole of dialkali metal salt is preferred. In some embodiments, the molar ratio of dialkali metal salt to the N-alkyl nitrophthalimide composition can be 1:1.5 to 1:2.5, or 1:1.7 to 1:2.3, or 1:1.8 to 1:2.2, or 1:1.9 to 1:2.1.

In some embodiments, the reaction to prepare the aromatic bisimide is conducted in the presence of a solvent. Any organic solvent which does not react with the reactants during the formation of the aromatic bisimide can be used in the reaction. In some embodiments, the solvent comprises a nonpolar organic solvent. Suitable nonpolar organic solvents include, but are not limited to, toluene, benzene, chlorobenzene, bromobenzene, dichlorobenzenes (e.g., ortho-, meta-, or para-dichlorobenzene), trichlorobenzenes (e.g., 1,2,4-trichlorobenzene), xylene (including m-xylene, o-xylene, p-xylene, and combinations comprising at least one of the foregoing), anisole, ethylbenzene, propylbenzene, mesitylene, and the like, or a combination comprising at least one of the foregoing. In some embodiments, the solvent can be toluene, benzene, chlorobenzene, ortho-dichlorobenzene, 1,2,4-trichlorobenzene, xylene, and the like, or a combination comprising at least one of the foregoing nonpolar organic solvents. In some embodiments, the solvent preferably comprises toluene.

The solvent can comprise a dipolar aprotic solvent. Suitable dipolar aprotic solvents can include, but are not limited to, dimethyl sulfoxide, dimethylacetamide, N-methylpyrrolidone, 1-cyclohexyl-2-pyrrolidone, N-isopropyl-pyrrolidone, tetramethylurea, dimethylformamide, sulfolane, N-methylcaprolactam, and the like, or a combination comprising at least one of the foregoing dipolar aprotic solvents. In some embodiments, the solvent can be a combination of a nonpolar organic solvent and a dipolar aprotic solvent. For example, a nonpolar organic solvent and a dipolar aprotic solvent can be present in a weight ratio of 1:99 to 99:1, or 5:95 to 95:5, or 10:90 to 90:10, or 20:80 to 80:20, or 30:70 to 70:30, or 40:60 to 60:40.

The solids content of the product mixture comprising the aromatic bisimide can be 5-90 wt %, or 10-90 wt %, or 10-80 wt %, or 10-70 wt %, or 10-60 wt %, or 10-50 wt %, or 10-40 wt %, or 10-30 wt %, or 10-20 wt %, or 5-80 wt %, or 5-70 wt %, or 5-60 wt %, or 5-50 wt %, or 5-40 wt %, or 5-30 wt % or 5-20 wt %; or 10-90 wt %, or 10-80 wt %, or 10-70 wt %, or 10-60 wt %, or 10-50 wt %, or 10-40 wt %, or 10-30 wt %, or 10-20 wt %; or 20-90 wt %, or 20-80 wt %, or 20-70 wt %, or 20-60 wt %, or 20-50 wt %, or 20-40 wt %, or 20-30 wt %.

In some embodiments, the reacting can be in the presence of a phase transfer catalyst. A wide variety of phase transfer catalysts can be used, for example various phosphonium, ammonium, guanidinium, and pyridinium salts can be used. The phase transfer catalyst can be a hexa($C_{1-12}$ alkyl) guanidinium salt, a tetra($C_{1-12}$ alkyl)ammonium salt, a tetra ($C_{1-12}$ alkyl) phosphonium salt, or a tetra($C_{6-20}$ aryl) phosphonium salt. For example, the phase transfer can be tetraethylammonium bromide, tetraethylammonium acetate, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium bromide, tetrabutylphosphonium chloride, hexaethylguanidinium chloride, and the like. A pyridinium salt, for example a bis-aminopyridinium salt can also be used.

The phase transfer catalyst can be a quaternary salt or a bis-quaternary salt. Among the quaternary salts that can be used are catalysts of the formula $(R^3)_4Q^+X$, wherein each $R^3$ is the same or different, and is a $C_{1-10}$ alkyl; Q is a nitrogen or phosphorus atom; and X is a halogen atom or a $C_{1-8}$ alkoxy or $C_{6-18}$ aryloxy. Exemplary phase transfer catalysts include $(CH_3(CH_2)_3)_4NX$, $(CH_3(CH_2)_3)_4PX$, $(CH_3(CH_2)_5)_4NX$, $(CH_3(CH_2)_6)_4NX$, $(CH_3(CH_2)_4)_4NX$, $CH_3(CH_3(CH_2)_3)_3NX$, and $CH_3(CH_3(CH_2)_2)_3NX$, wherein X is Cl$^-$, Br$^-$, a $C_{1-8}$ alkoxy or a $C_{6-18}$ aryloxy.

Among the bis-quaternary salts that can be used are those of the formula $(R^4)_kQ^+(R^3)_m{}^+Q(R^4)_k (X^2)_2$ wherein each $R^3$ is independently a divalent $C_{1-60}$ hydrocarbon group, all $R^3$ taken together contain 4-54 carbon atoms, each $R^4$ is independently a $C_{1-12}$ hydrocarbon group, Q is nitrogen or phosphorus, preferably nitrogen, $X^2$ is an organic or inorganic anionic atom or group, k is an integer from 1-3, and m is 4-k, wherein at least three of $R^3$ and $R^4$ groups attached to each Q atom are aliphatic or alicyclic. In particular, each $R^3$ can be a divalent $C_{1-18}$ alkylene, $C_{3-8}$ cycloalkylene, or $C_{6-18}$ aromatic group such as ethylene, propylene, trimethylene, tetramethylene, hexamethylene, octamethylene, decamethylene, dodecamethylene, cyclohexylene, phenylene, tolylene, or naphthylene, or a $C_{3-12}$ divalent heterocyclic group derived from a compound such as pyridine or indole. In some embodiments, each $R^3$ is $C_{1-12}$ alkylene, specifically $C_{3-8}$ alkylene. Preferably, only one $R^3$ group is present (i.e., m is 1 and each k is 3) and it contains 5-10, specifically 6 carbon atoms. Illustrative $R^4$ groups are methyl, ethyl, n-propyl, isopropyl, n-butyl, isobutyl, n-hexyl, n-heptyl, cyclopentyl, cyclohexyl, methylcyclohexyl, phenyl, tolyl, 2-(1,4-dioxanyl) and 2-furyl. Preferably, the $R^4$ groups are all alkyl, for example $C_{1-4}$ n-alkyl groups. The $X^2$ can be any anion that is stable under the conditions used; suitable anions include chloride, bromide, sulfate, p-toluenesulfonate, and methanesulfonate, preferably bromide. The value of the integer k can be from 1-3, and the value of m is 4-k. In some embodiments, each k is 3 and m is 1. In the some embodiments, all of the $R^3$ and $R^4$ groups are aliphatic. Illustrative bis-quaternary salts of this type include those in which $R^3$ is a polymethylene chain from trimethylene to dodecamethylene, each $R^4$ is either n-butyl or n-hexyl, Q is nitrogen, $X^2$ is bromide, each k is 2 and m is 2; the compound in which each $R^3$ is ethylene, $R^4$ is n-butyl, Q is nitrogen, $X^2$ is bromide, each k is 1 and m is 3; and the compound in which $R^3$ is hexamethylene, each $R^4$ is n-butyl, Q is phosphorus, $X^2$ is bromide, each k is 3 and m is 1.

Quaternary salts that can be used as phase transfer catalysts include quaternary salts of dihydroxy aromatic compounds as described in U.S. Pat. No. 5,756,843 to Webb et al. For example, a quaternary salt of a dihydroxy aromatic compound can be of the formula $A^+(O—Z—O)_2H_3$, wherein A is a monocationic carbon- and nitrogen- or phosphorus containing group (i.e., a group having a single positive charge comprising carbon and nitrogen or carbon and phosphorus). The group A comprises 1-6 $C_{2-12}$ alkyl groups. In some embodiments, A preferably comprises nitrogen. In some embodiments, A can be a tetra($C_{2-12}$alkyl)ammonium or tetra($C_{2-12}$alkyl)phosphonium group, for example tetraethylammonium, tetra-n-butylammonium, tetra-n-butylphosphonium and diethyl di-n-butylammonium. In some embodiment, A is preferably a hexa($C_{2-12}$alkyl)guanidinium group, for example hexaethylguanidinium, hexa-n-butylguanidinium, or tetraethyldi-n-butylguanidinium. Z is an aromatic $C_{6-24}$ monocyclic or polycyclic moiety optionally substituted with 1-6 $C_{1-8}$ alkyl groups, 1-8 halogen atoms, or a combination comprising at least one of the foregoing. In some embodiments, Z is of formula (IIa) as described below. Z is 2,2-(4-phenylene)isopropylidene (i.e., the dihydroxy aromatic compound from which Z is derived is 2,2-bis-(4-hydroxyphenyl)propane or bisphenol A). The quaternary salts of dihydroxy aromatic compounds can be prepared, for example, by the reaction of a dihydroxyaromatic compound of the formula HO—Z—OH with an alkali metal hydroxide and a quaternary salt of the formula $A^+X$. The group X can be as described above, and is a halide, or bromide or chloride and most preferably chloride. Typical reaction temperatures are 1-125° C., preferably 10-50° C., and preferably under an inert atmosphere such as nitrogen or argon.

In some embodiments, the phase transfer catalyst is preferably a hexa($C_{1-12}$alkyl)guanidinium salt, for example hexaethylguanidinium chloride.

The phase transfer catalyst can be present in an amount of 0.1-10 mole percent (mol %), or 1-10 mol %, or in some embodiments 0.5-2.0 mol %, based on the total moles of the dialkali metal salt of the dihydroxy aromatic compound. In some embodiments, the phase transfer catalyst can be present in an amount of greater than 1 to 10 mol %, based on the total moles of the dialkali metal salt of the dihydroxy aromatic compound. For example, the phase transfer catalyst can be present in an amount of 0.1-9 mol %, or 0.1-7 mol %, or 0.1-5 mol %, or 0.1-3 mol %, or 0.1-1 mol %, or 0.1-0.5 mol %, or 0.5-10 mol %, or 1-10 mol %, or 2-10 mol %, or 3-10 mol %, or 2-8 mol %, or 2-5 mol %, or 3-5 mol %, or 3-8 mol %, or 5-10 mol %, or 7-10 mol %, or 9-10 mol %.

In some embodiments, the phase transfer catalyst can be present in an amount of 0.5-1.5 mol %, or 0.6-1.2 mol %. It has been found that the amount of catalyst can affect the amount of the DNPI that can be present in the N-alkyl nitrophthalimide composition, and still produce low color and high yield compositions comprising bisimides, as well as low color polyetherimides. For example, an amount of up to 2.0 mol % allows the presence of up to 7000 ppm of the 4-hydroxy-3,5-dinitro-N—($C_{1-13}$ alkyl)phthalimide, specifically DNPI, and nonetheless provides aromatic bisimides with low color and in good yields. Higher amounts of catalyst (e.g., 3 mol %, or 3-5 mol %) can allow the presence of even higher amounts of the 4-hydroxy-3,5-dinitro-N—($C_{1-13}$ alkyl)phthalimide, specifically DNPI, for example 7000 to 10000 ppm, and provide aromatic bisimides with low color and in good yields.

The bisimide can be recovered from the product mixture and purified by a variety of procedures. One procedure includes dissolution of the bisimide in an organic solvent such as toluene and then washing or extracting with alkali solution containing 0.1-10 wt %, or 1-5 wt % alkali, to remove by-products, e.g., monoimides, and the like, phase transfer catalyst, and unreacted starting materials. In some embodiments, the volumetric ratio of the alkali solution to the organic phase (e.g., the bisimide in organic solvent) during the washing or extracting can be 1:5 to 1:15, or 1:5 to 1:10, or 1:6 to 1:9, or 1:6 to 1:8.

The aromatic bisimides prepared according to the above method can be obtained in a yield of greater than 75%, or greater than 85%, or greater than 90%. For example, the aromatic bisimides prepared according to the above method can be obtained in a yield of 75 to 99%, or 85 to 99%, or 90-99%, or 95-99%, or 97-99%, or 98-99%; or 75 to 99.5%, or 85 to 99.5%, or 90-99.5%, or 95-99.6%, or 97-99.5%, or 98-99.5%, or 99-99.6%; or 75 to 99.6%, or 85 to 99.6%, or 90-99.6%, or 95-99.6%, or 97-99.6%, or 98-99.6%, or 99-99.6%; or 75-99.8%, or 85-99.8%, or 90-99.8%. The preferred yields are 90-99.8%, or 95-99.8%, or 97-99.8%, or 98-99.8%, or 99-99.8%.

After recovery, the aromatic bisimide can be of high or low color, as indicated by yellowness index (YI). YI is a value calculated from spectrophotometric data that describes the color of a test sample as being clear or white (low YI) versus being more yellow (high YI). Sample handling and preparation can affect the test results. YI of the aromatic bisimide can be measured according to ASTM D1925, by dissolving 0.5 g of aromatic bisimide in 10 milliliters of methylene chloride, and measuring the YI of the resulting solution, for example on an Xrite 7000 Color Eye device (Xrite, Incorporated). In some embodiments, the YI of the aromatic bisimide can be 75 or less, or 50 or less, for example 25-75 or 25-50. In preferred embodiments, the YI of the aromatic bisimide can be less than 25, or less than 10, or less than 9, or less than 8, or less than 7, or less than 6, or less than 5, determined in accordance with ASTM D-1925. For example, the aromatic bisimide can have a YI of 1-75, or 1-50, or 1-25, or 5-25, or 10-25, or 15-25, or 1-20, or 1-15, or 5-15, or 1-10, or 1-9, or 1-8, or 1-7, or 1-6, or 1-5, or 1-4, or 1-3, or 2-9, or 2-8, or 2-7, or 2-6, or 2-5, or 2-4, or 3-9, or 3-8, or 3-7, or 3-6, or 3-5, or 4-9, or 4-8, or 4-7, or 4-6, or 5-9, or 5-8, or 5-7, or 6-9, or 6-8, or 7-9, determined in accordance with ASTM D-1925.

In an embodiment, the method for producing an aromatic bisimide preferably comprises reacting a dialkali metal salt of a dihydroxy aromatic compound with an N-alkyl nitrophthalimide composition in the presence of a hexaethylguanidinium chloride phase transfer catalyst and under conditions effective to form a product mixture comprising the aromatic bisimide, wherein the N-alkyl nitrophthalimide composition comprises 4-nitro-N—($C_{1-13}$ alkyl)phthalimide, 3-nitro-N—($C_{1-13}$ alkyl)phthalimide, or a combination comprising at least one of the foregoing; and 4-hydroxy-3,5-dinitro-N—($C_{1-13}$ alkyl)phthalimide in an amount as described above, for example up to 10000 ppm, or 10-10000 ppm, or 10 to 7000 ppm, or 10 to 6000 ppm, or 10 to 3000 ppm, wherein the aromatic bisimide is obtained in a yield of greater than 75%, or greater than 85%, or 90-100%, or 95-100%, or 98-100%, and the aromatic bisimide has a YI of less than 75, or less than 50, or less than 25, as determined according to ASTM D-1925. It is unexpected that these high yields can be achieved in the presence of the higher amounts of the 4-hydroxy-3,5-dinitro-N—($C_{1-13}$ alkyl)phthalimide. Where lower amounts of the 4-nitro-hydroxy-3,5-dinitro-N—($C_{1-13}$ alkyl)phthalimide are desired in the aromatic bisimide product, the 4-nitro-hydroxy-3,5-dinitro-N—($C_{1-13}$ alkyl)phthalimide can be removed from the 4-nitro-N—($C_{1-13}$ alkyl)phthalimide, 3-nitro-N—($C_{1-13}$ alkyl)phthalimide mixture by adding water to the mixture to form a precipitate, then isolating the 4-nitro-N—($C_{1-13}$ alkyl)phthalimide, 3-nitro-N—($C_{1-13}$ alkyl)phthalimide mixture by filtration, removing the more soluble 4-nitro-hydroxy-3,5-dinitro-N—($C_{1-13}$ alkyl)phthalimide in the filtrate. For example, the 4-nitro-N—($C_{1-13}$ alkyl)phthalimide, 3-nitro-N—($C_{1-13}$ alkyl)phthalimide, and 4-hydroxy-3,5-dinitro-N—($C_{1-13}$ alkyl)phthalimide can be precipitated, the precipitate isolated (for example by filtration or centrifugation), and then washed with water. Depending on the extent of the water washing and the temperature of the water, the isolated 4- and 3-nitro-N—($C_{1-13}$ alkyl)phthalimide precipitate can contain the the 4-hydroxy-3,5-dinitro-N—($C_{1-13}$ alkyl)phthalimide, specifically DNPI, in an amount of 1-10000 ppm, or 50-10000 ppm, or 100-10000 ppm, or 500-10000 ppm, or 1000-10000 ppm; 1-8000 ppm, or 50-8000 ppm, or 100-8000 ppm, or 500-8000 ppm, or 1000-8000 ppm or 1-8000 ppm, or 50-8000 ppm, or 100-7000 ppm, or 500-7000 ppm, or 1000-7000 ppm; or 1-6000 ppm, or 50-6000 ppm, or 100-6000 ppm, or 500-6000 ppm, or 1000-6000 ppm; or 1-4000 ppm, or 50-4000 ppm, or 100-4000 ppm, or 500-4000 ppm, or 1000-4000 ppm; or 1-3000 ppm, or 50-3000 ppm, or 100-3000 ppm, or 500-3000 ppm, or 1000-3000 ppm. In some embodiments, the 4-hydroxy-3,5-dinitro-N—($C_{1-13}$ alkyl)phthalimide, specifically DNPI, is present in an amount of 1-10000, or 1-8000 ppm, or 1-6500, or 1-4000, or 1-3000, or 500-6500, or 500-3000 ppm, or 1000-3000 ppm. In another embodiment, the 4-hydroxy-3,5-dinitro-N—($C_{1-13}$ alkyl)phthalimide, specifically DNPI, is present in an amount of 1-6000 ppm, or 1-5000 ppm, or 500-3000 ppm, or 100-3000 ppm, or 500-3000 ppm, or 1000-3000 ppm after the product mixture has been washed, as described above.

In some embodiments, after recovery of the aromatic bisimide, the aromatic bisimide can be substantially free of 4-hydroxy-3,5-dinitro-N—($C_{1-13}$ alkyl)phthalimide. The term "substantially free" means that the aromatic bisimide has less than 10 ppm, or less than 1 ppm of 4-hydroxy-3,5-dinitro-N—($C_{1-13}$ alkyl)phthalimide. In some embodiments, any 4-hydroxy-3,5-dinitro-N—($C_{1-13}$ alkyl)phthalimide is present in an amount that is not detectable, for example by a high performance liquid chromatography (HPLC) method after recovery.

The dialkali metal salt of the dihydroxy aromatic compound is of formula (I)

$$M^+\text{—O—Z—O}^-M \qquad (I)$$

wherein M is an alkali metal and Z is an aromatic $C_{6-24}$ monocyclic or polycyclic moiety optionally substituted with 1-6 $C_{1-8}$ alkyl groups, 1-8 halogen atoms, or a combination comprising at least one of the foregoing. The alkali metal M can be, for example, lithium, sodium, potassium, or a combination comprising at least one of the foregoing. In some embodiments, M is sodium. Exemplary groups Z include groups derived from an aromatic dihydroxy compound of formula (II)

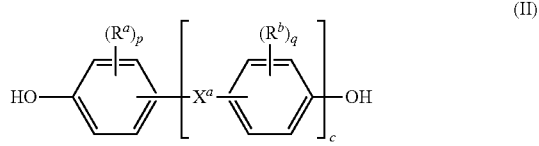

wherein $R^a$ and $R^b$ can be the same or different and are a halogen atom or a monovalent $C_{1-6}$ alkyl group, for example; p and q are each independently integers of 0-4; c is 0-4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of formula

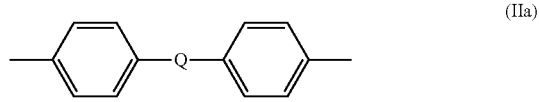

wherein Q is —O—, —S—, —C(O)—, —S$_2$—, —SO—, or —C$_y$H$_{2y}$— wherein y is an integer from 1-5 or a halogenated derivative thereof. Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In some embodiments, Z is 2,2-(4-phenylene)isopropylidene (i.e., the dihydroxy aromatic compound from which the dialkali metal salt is derived is 2,2-bis-(4-hydroxyphenyl) propane or bisphenol A, such that Q in formula (IIa) is 2,2-isopropylidene).

The N-alkyl nitrophthalimide composition comprises an N-alkyl nitrophthalimide of formula (III)

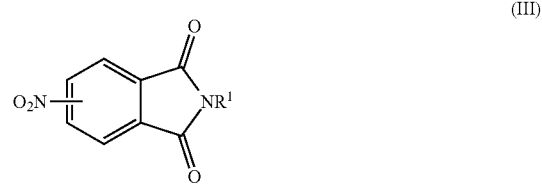

wherein $R^1$ is a monovalent $C_{1-13}$ organic group, preferably a $C_{1-4}$ alkyl group, for example a methyl group. In some embodiments, the N-alkyl nitrophthalimide composition comprises 4-nitro-N—($C_{1-13}$ alkyl)phthalimide, preferably 4-nitro-N-methylphthalimide. In some embodiments, the N-alkyl nitrophthalimide composition comprises 3-nitro-N—($C_{1-13}$ alkyl)phthalimide, specifically 3-nitro-N-methylphthalimide. In some embodiments, the N-alkyl nitrophthalimide composition comprises 4-nitro-N—($C_{1-13}$ alkyl) phthalimide and 3-nitro-N—($C_{1-6}$ alkyl)phthalimide, specifically 4-nitro-N-methylphthalimide and 3-nitro-N-methylphthalimide. When the N-alkyl nitrophthalimide composition comprises 4-nitro-N—($C_{1-13}$ alkyl)phthalimide and 3-nitro-N—($C_{1-6}$ alkyl)phthalimide, the 4-nitro-N—($C_{1-13}$ alkyl)phthalimide and 3-nitro-N—($C_{1-6}$ alkyl)phthalimide can be present in any ratio. For example, the ratio of 4-nitro-N—($C_{1-13}$ alkyl)phthalimide to 3-nitro-N—($C_{1-6}$ alkyl)phthalimide can be 0.001:99.999 to 99.999:0.001, or 0.01:99.99 to 99.99:0.01, or 0.1:99.9 to 99.9:0.1. For example, the ratio of 4-nitro-N—($C_{1-13}$ alkyl)phthalimide to 3-nitro-N—($C_{1-6}$ alkyl)phthalimide can be 1:99 to 99:1, or 10:90 to 90:10, or 20:80 to 80:20, or 30:70 to 70:30, or 40:60 to 60:40. In some embodiments, the ratio of 4-nitro-N—($C_{1-13}$ alkyl)phthalimide to 3-nitro-N—($C_{1-6}$ alkyl)phthalimide can be at least 50:50, for example 50:50 to 99.999:0.001, or 50:50 to 99.999:0.001, or 60:40 to 99.99:0.01, or 70:30 to 99.99:0.01, or 80:20 to 99.99:0.01, or 90:10 to 99.99:0.01, or 92:8 to 99.99:0.01. In an embodiment, the ratio of 4-nitro-N—($C_{1-13}$ alkyl)phthalimide to 3-nitro-N—($C_{1-6}$ alkyl)phthalimide can be 90:10 to 99.99:0.01, or 95:5 to 99.99:0.01, or 90:10 to 99.9:0.1, or 95:5 to 99.9:0.1.

The N-alkyl nitrophthalimide composition also comprises 4-hydroxy-3,5-dinitro-N—($C_{1-13}$ alkyl)phthalimide, specifically DNPI. The 4-hydroxy-3,5-dinitro-N—($C_{1-13}$ alkyl) phthalimide can be present in an amount of 1-10000 ppm, or 50-10000 ppm, or 100-10000 ppm, or 500-10000 ppm, or 1000-10000 ppm; 1-8000 ppm, or 50-8000 ppm, or 100-8000 ppm, or 500-8000 ppm, or 1000-8000 ppm or 1-8000 ppm, or 50-8000 ppm, or 100-7000 ppm, or 500-7000 ppm, or 1000-7000 ppm; or 1-6000 ppm, or 50-6000 ppm, or 100-6000 ppm, or 500-6000 ppm, or 1000-6000 ppm; or 1-4000 ppm, or 50-4000 ppm, or 100-4000 ppm, or 500-4000 ppm, or 1000-4000 ppm; or 1-3000 ppm, or 50-3000 ppm, or 100-3000 ppm, or 500-3000 ppm, or 1000-3000 ppm, each based on the total weight of the N-alkyl nitrophthalimide composition. In another embodiment, the 4-hydroxy-3,5-dinitro-N—($C_{1-13}$ alkyl)phthalimide is present in an amount of 1-35000 ppm, or 50-35000 ppm, or 100-35000 ppm, or 500-35000 ppm, or 1000-35000 ppm, or 5000-35000 ppm, or 10000 to 35000 ppm, or 20000 to 35000 ppm, or 1-3000 ppm, or 50-3000 ppm, or 100-3000 ppm, or 500-3000 ppm, or 1000-3000 ppm, 1-5000 ppm, or 100-5000 ppm, or 200-5000 ppm, or 500-5000 ppm, or 1000-5000 ppm, or 2500-5000 ppm, or 3500 to 5000 ppm, or 50 to 3500 ppm, or 1-2500 ppm, or 1-1000 ppm, or 1-100 ppm, or 1-200 ppm, or 1-500 ppm, or 100-200 ppm, or 100-500 ppm, or 100-1000 ppm, or 100-2500 ppm, or 100-3500 ppm, or 200-500 ppm, or 200-1000 ppm, or 200-2500 ppm, or 200-3500 ppm, or 500-1000 ppm, or 500-2500 ppm, or 500 to 3500 ppm, each based on the total weight of the N-alkyl nitrophthalimide composition.

The aromatic bisimide is of formula (IV)

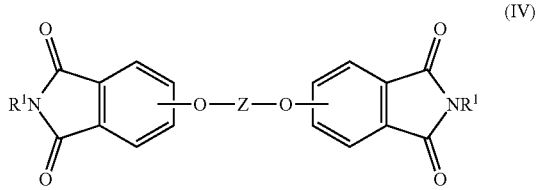

(IV)

wherein $R^1$ is a $C_{1-13}$ organic group, or a $C_{1-4}$ alkyl group, preferably a methyl group, and Z is as described in formula (I). In some embodiments, Z is a divalent group of formula (IIa), as described above, preferably 2,2-(4-phenylene)isopropylidene (i.e., the dihydroxy aromatic compound from which the dialkali metal salt is derived is 2,2-bis-(4-hydroxyphenyl)propane or bisphenol A). In some embodiments, the aromatic bisimide comprises 4,4'-bisphenol-A-bis-N-methylphthalimide, 3,4'-bisphenol-A-bis-N-methylphthalimide, 3,3'-bisphenol-A-bis-N-methylphthalimide, or a combination comprising at least one of the foregoing.

A method for the manufacture of a polyetherimide is further disclosed. The method includes contacting the aromatic bisimide of formula (IV) prepared according to the above-described method with a phthalic anhydride in the presence of a catalyst to provide an aromatic bis(ether phthalic anhydride) of formula (V)

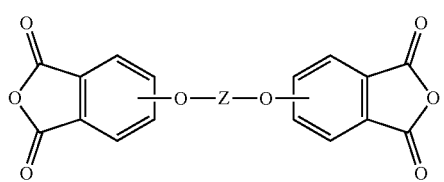

(V)

wherein Z is an aromatic $C_{6-24}$ monocyclic or polycyclic moiety optionally substituted with 1 to 6 $C_{1-8}$ alkyl groups, 1-8 halogen atoms, or a combination comprising at least one of the foregoing, as described above. The divalent bonds of the —O—Z—O— group are in the 3,3', 3,4', 4,3', or the 4,4' positions. In some embodiments, Z is 2,2-(4-phenylene) isopropylidene. Illustrative examples of aromatic bis(ether phthalic anhydride)s include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride, as well as various combinations thereof.

The catalyst can be a tertiary amine. Among tertiary amines that can be used as catalysts are aliphatic tertiary amines such as triethylamine and tributylamine, cycloaliphatic tertiary amines such as N,N-diethyl-cyclohexylamine, and aromatic tertiary amines such as N,N-dimethylaniline. In some embodiments, the catalyst comprises a $C_{1-20}$ trialkylamine, for example triethylamine, tributylamine, and the like, or a combination comprising at least one of the foregoing. In an embodiment, the catalyst is triethylamine. In some embodiments, the contacting can occur in the presence of 0.5-15 mole percent of the catalyst with respect to the anhydride.

The aromatic bisimide and the phthalic anhydride are contacted under conditions that are generally known to be effective to provide the aromatic bis(ether phthalic anhydride). For example, the phthalic anhydride can be present in a molar excess compared to the aromatic bisimide, for example 3-8 molar excess of phthalic anhydride relative to aromatic bisimide. The contacting can further be in the presence of a solvent, for example, an aromatic solvent including, but not limited to, benzene, toluene, xylene, chlorobenzene, and o-dichlorobenzene, preferably toluene. In some embodiments, the solvent can comprise a solvent mixture, for example water and toluene. The contacting can be at a temperature of 100-300° C., or 100-280° C., or 100-250° C., or 110-240° C., or 120-230° C., or 130-220° C., or 150-210° C., or 150-250° C., or 170-260° C. The contacting can be at superatmospheric pressure, for example 200-700 pounds per square inch (psi), or 200-400 psi, or 200-600 psi, or 300-500 psi, or 300-600 psi, or 300-700 psi, or 400-600 psi, or 500-700 psi. The contacting of the aromatic bisimide and the phthalic anhydride can be carried out for 0.5-3 hours, preferably with agitation (e.g., stirring).

The method for manufacturing the polyetherimide further comprises contacting the aromatic bis(ether phthalic anhydride) of formula (V) with an organic diamine of formula (VI)

$$H_2N—R—NH_2 \qquad (VI)$$

to provide the polyetherimide. In formula (VI), R is a substituted or unsubstituted divalent organic group, such as a substituted or unsubstituted $C_{6-20}$ aromatic hydrocarbon group, a substituted or unsubstituted straight or branched chain $C_{4-20}$ alkylene group, a substituted or unsubstituted $C_{3-8}$ cycloalkylene group, in particular a halogenated derivative of any of the foregoing. Specifically is in particular a divalent group of one or more of the following formulas

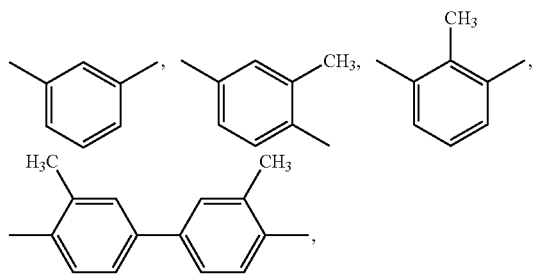

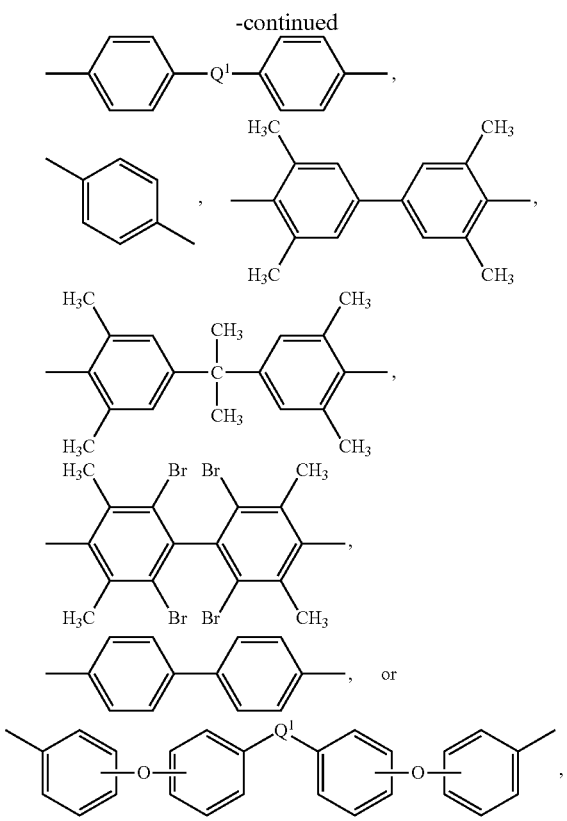

wherein $Q^1$ is —O—, —S—, —C(O)—, —SO$_2$—, —SO—, —P(R$^a$)(=O)— wherein R$^a$ is a C$_{1-8}$ alkyl or C$_{6-12}$ aryl, —C$_y$H$_{2y}$— wherein y is an integer from 1-5 or a halogenated derivative thereof (which includes perfluoroalkylene groups), or —(C$_6$H$_{10}$)$_z$— wherein z is an integer from 1-4. In an embodiment R is m-phenylene, p-phenylene, or a diarylene sulfone, in particular bis(4,4'-phenylene)sulfone.

Examples of organic diamines include 1,4-diaminobutane, 1,5-pentanediamine, 1,6-hexanediamine, 1,7-heptanediamine, 1,8-octanediamine, 1,9-nonanediamine, 1,10-decanediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis(p-amino-t-butylphenyl) ether, bis(p-methyl-o-aminophenyl) benzene, bis(p-methyl-o-aminopentyl) benzene, 1,3-diamino-4-isopropylbenzene, bis(4-aminophenyl) sulfide, bis-(4-aminophenyl) sulfone (also known as 4,4'-diaminodiphenyl sulfone (DDS)), and bis(4-aminophenyl) ether. C$_{1-4}$ alkylated or poly(C$_{1-4}$)alkylated derivatives of any of the foregoing can be used, for example a polymethylated 1,6-hexanediamine. Regioisomers of any of the foregoing can also be used. Combinations of these compounds can also be used. In some embodiments the organic diamine is m-phenylenediamine, p-phenylenediamine, 4,4'-diaminodiphenyl sulfone, 3,4'-diaminodiphenyl sulfone, 3,3'-diaminodiphenyl sulfone, or a combination comprising at least one of the foregoing.

The contacting of the aromatic bis(ether phthalic anhydride) with the organic diamine can be in the presence of a solvent, for example, N-methylpyrrolidone, dimethylacetamide, dimethylformamide, cresol, veratrole, phenetole, dimethylsulfoxide, trichloromethane, acetone, methanol, ethanol, toluene, benzene, chlorobenzene, bromobenzene, dichlorobenzenes, trichlorobenzenes (e.g., 1,2,4-trichlorobenzene), xylene (including m-xylene, o-xylene, p-xylene, and combinations comprising at least one of the foregoing), anisole, ethylbenzene, propylbenzene, mesitylene, and the like, or a combination comprising at least one of the foregoing. Sufficient solvent is generally utilized to provide a solids content of 1-90%, or 10-90%, or 30-90%, or 50-90%, or 70-90%, or 1-10%, or 10-30%, or 10-50%, or 10-70%, or 10-80%, or 20-40%, or 20-60%, or 20-80%, or 30-50%, or 30-70%, or 30-80%, or 40-60%, or 40-80%, or 50-80%. In some embodiments, the solids content can be 15-60%.

In some embodiments, the contacting can be in the presence of an endcapping agent. The endcapping agent limits molecular weight growth rate, and thus can be used to control molecular weight in the polyetherimide. Exemplary an endcapping agent include certain monoamines (for example aniline), monoanhydrides (for example phthalic anhydride), and the like. In an embodiment, the endcapping agent is phthalic anhydride, such that the resulting polyetherimide comprises phthalimide as an endcap to the polymer chain. It should be understood, however, that the polyetherimides disclosed herein can be produced having any desired weight average molecular weight (Mw) with any endcap.

The contacting of the aromatic bis(ether phthalic anhydride) with the organic diamine can be at a temperature of 100-250° C., or 120-230° C., or 150-210° C., or 150-250° C., and can be carried out for 0.5-10 hours, preferably with agitation (e.g., stirring). To avoid deleterious oxidation reactions, the contacting of the aromatic bis(ether phthalic anhydride) with the organic diamine can be blanketed under an inert gas. Examples of such gases are dry nitrogen, helium, argon and the like. Dry nitrogen can be preferred. The reaction can be run at atmospheric to superatmospheric pressure.

Alternatively, a method for the manufacture of a polyetherimide comprises hydrolyzing the aromatic bisimide of formula (IV) prepared by the above method under conditions effective to provide the corresponding tetraacid of formula (VII)

(VII)

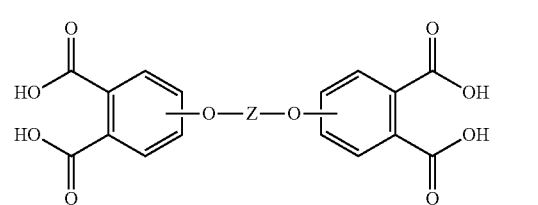

wherein Z is as defined above. In some embodiments, Z is 2,2-(4-phenylene)isopropylidene.

Hydrolyzing the aromatic bisimide to provide the corresponding tetraacid can be under conditions effective to provide the tetraacid, for example, as described in U.S. Pat. No. 3,879,428. For example, the aromatic bisimide can be hydrolyzed in an aqueous alkaline solution, for example comprising an alkali metal hydroxide, preferably sodium hydroxide. Reaction time can vary from 1-24 hours or more depending upon reactants, degree of agitation, temperature, pressure, and the like. The organic amine by-product can be removed by standard procedures, such as steam distillation, decantation (when butyl-derived materials are used), and the like. In addition, the rate of hydrolysis is accelerated by carrying out the reaction at above atmospheric pressures, and at temperatures of 100-220° C. For example, hydrolysis can be at a temperature of 120-220° C., or 140-220° C., or 160-220° C., or 180-220° C., or 200-220° C., or 100-210° C., or 100-190° C., or 100-170° C., or 100-150° C., or 100-130° C. The hydrolysis can be at a pressure of 0 MPa-2 MPa. The hydrolyzed bisimide can be acidified with an acidic aqueous solution, for example comprising a mineral acid, for example sulfuric acid, hydrochloric acid, and the like, to provide the tetraacid.

The tetraacid can be condensed (i.e., dehydrated) under conditions effective to provide an aromatic bis(ether phthalic anhydride) of formula (V). Condensing the tetraacid to provide the corresponding aromatic bis(ether phthalic anhydride) can be under conditions to provide the aromatic bis(ether phthalic anhydride). For example, the tetraacid can be condensed by refluxing in the presence of a dehydrating agent, for example acetic anhydride. In some embodiments, a temperature of 100-225° C. and a pressure of 0 MPa-1 MPa can be used. The aromatic bis(ether phthalic anhydride) can optionally be isolated using any isolation techniques that are generally known, for example, filtration. Alternatively, the aromatic bis(ether phthalic anhydride) can be used directly for the preparation of the polyetherimide without further purification or isolation.

The method for the manufacture of the polyetherimide via the tetraacid (VII) can further comprise contacting the aromatic bis(ether phthalic anhydride) (V) (obtained by dehydrating the tetraacid as described above) with an organic diamine of formula (VI) to provide the polyetherimide. The contacting can be in the presence of a solvent or an endcapping agent as described above. Alternatively, in some embodiments, the polyetherimide can be prepared by contacting the tetraacid (VII) directly with an organic diamine (VI) to provide the polyetherimide (i.e., dehydration of the tetraacid to provide the corresponding aromatic bis(ether phthalic anhydride) is not required).

The polyetherimide prepared according to either of the above-described methods for the manufacture of a polyetherimide can have a YI of less than 120, or less than 110, or less than 100, or less than 90, or less than 80, or less than 70, or less than 60, or less than 50. For example, the polyetherimide can have a YI of 40-120, or 40-110, or 40-100, or 40-90, or or 40-80, or 40-70, or 40-60, or 40-50. In some embodiments, the polyetherimide can have a YI of 45-120, or 45-100, or 45-90, or 45-80, or 45-70, or 45-60, or 45-55. In other embodiments, the polyetherimide can have a YI of 50-120, or 50-100, or 50-90, or 50-80, or 50-70, or 50-60 In still other embodiments, the polyetherimide can have a YI of 60-120, or 60-100, or 60-90, or 60-80 or 60-70; or 70-120, or 70-100, or 70-90 or 70-80; or 80-120, or 80-100. In any of the foregoing embodiment, the YI of the polyetherimide can be determined according to ASTM D1925, at a thickness of 3.2 millimeters.

The polyetherimide prepared according to the above-described methods comprises repeating units of formula (VIII)

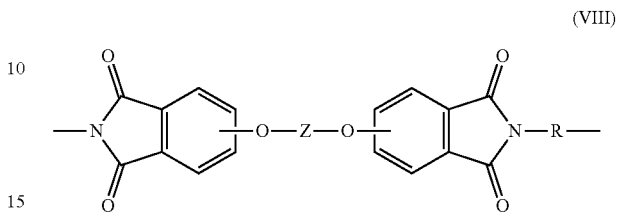

wherein Z is as defined in formula (I) and each R is the same or different, and is as defined in formula (VI). In an embodiment, in formula (VIII) R is m-phenylene, p-phenylene, 4,4'-diaminodiphenyl sulfone, 3,4'-diaminodiphenyl sulfone, 3,3'-diaminodiphenyl sulfone, or a combination comprising at least one of the foregoing and Z is a divalent group of formula (IIa) wherein Q is 2,2-isopropylidene.

An article comprising the polyetherimides prepared as described above is further disclosed. Articles including the polyetherimide can be prepared by any number of methods including shaping, foaming, extruding, thermoforming, spinning, or molding. Articles can be in the form, for example, of fibers, hollow fibers, hollow tubes, sheets, films, multilayer sheets, multilayer films, molded parts, extruded profiles, coated parts, foams, filaments, or powders. In some embodiments, the article is a fiber, a film, a sheet, a foam, a filament, a molded article, an extruded article, or a powder.

Another aspect of the present disclosure is a mixed acid nitration process for the preparation of an N-alkyl nitrophthalimide composition. The process comprises contacting an N-alkyl phthalimide with nitric acid and sulfuric acid to provide a nitration product mixture as described above. The nitro-N-alkylphthalimide can be isolated from the mixture and optionally further purified using a series of precipitation, washing, and extraction techniques as further described below. The isolated and purified composition can be used in any of the foregoing processes for manufacture of the aromatic bisimide (IV), the aromatic bis(ether anhydride) (V), or the polyetherimide (VIII).

In particular, the mixed acid nitration process comprises contacting an N—($C_{1-13}$ alkyl)phthalimide with nitric acid and sulfuric acid to provide an N-alkyl nitrophthalimide composition comprising 4-nitro-N—($C_{1-13}$ alkyl)phthalimide, 3-nitro-N—($C_{1-13}$ alkyl)phthalimide, or a combination comprising at least one of the foregoing, and 4-hydroxy-3,5-dinitro-N—($C_{1-13}$ alkyl)phthalimide. The nitric acid and sulfuric acid and the N-alkyl phthalimide can be mixed together in a reactor, preferably a reactor equipped with a stirrer and means for heating or cooling the reactor. For safety and process reasons, it is preferred that the N-alkyl phthalimide is first dissolved in concentrated sulfuric acid to achieve a 10-40 wt %, or 15-40 wt %, or 20-40 wt %, or 25-35 wt %, or 28-32 wt % solution of N-alkyl phthalimide in the sulfuric acid. Concentrated nitric acid can be slowly added to the sulfuric acid solution. The nitric acid can be added such that the N-alkyl phthalimide and the nitric acid are present in the mixed acid nitration product mixture in a molar ratio of 1:1 to 1:3, or 1:1 to 1:2, or 1:1 to 1:1.5, or 1:1.1 to 1:1.3. The addition of nitric acid constitutes an exothermic reaction, which is preferably controlled by cooling the reactor. The reactor can be such as to allow for either batch or continuous processing. The N-alkyl phthalimide can be added in any suitable form, e.g., powder, flake, or liquid.

As discussed above, the acid used for the mixed acid nitration process includes concentrated nitric acid and concentrated sulfuric acid. The concentrated nitric acid can be 60-100%, or 70-100%, or 80-100%, or 90-100%, or 95-100%, or 98-100%, or 60-70%, or 60-80%, or 60-90%, or 60-98%, or 99% by weight concentrated nitric acid. The concentrated sulfuric acid can be 70-100%, or 80-100%, or 85-100%, or 90-100%, or 95-100%, or 98-100%, or 70-80%, or 70-85%, or 70-90%, or 70-95%, or 70-98% by weight concentrated sulfuric acid. In some embodiments, the concentrated sulfuric acid can be greater than 100% concentrated sulfuric acid, e.g., by the addition oleum, also known as fuming sulfuric acid. Thus, the concentrated sulfuric acid can be 70-105%, or 80-105%, or 85-105%, or 90-105%, or 95-105%, or 98-105%, or 95-103%, or 98-103%, or 99-103%, or 100-103% by weight concentrated sulfuric acid.

The nitration can be carried out at a temperature of less than or equal to 60° C., for example 25-60° C., or 30-60° C., or 35-60° C., or 40-60° C., or 45-55° C. In an embodiment, the nitration is carried out at a temperature of 40-55° C. Temperatures outside the range of temperatures disclosed above also can be employed, however, lower temperatures can result in a reaction rate that is too slow to be cost effective, and higher temperatures require operation at above atmospheric pressure to prevent boiling and subsequent loss of nitric acid. In particular, temperatures greater than 60° C. and molar ratios of N-alkyl phthalimide to nitric acid greater than 1:1.3 are generally avoided, mainly for safety reasons. The percent solids in the mixed acid nitration method can be 10-50%, or 10-40%, or 10-30%, or 10-20%, or 20-50%, or 20-40%, or 20-30%, or 30-40%, or 30-50%, or 40-50%, or 25-35% by weight, based on the total weight of the nitration product mixture. The pressure range under which the nitration process operates can vary from slight vacuum to above atmospheric pressure. Such conditions, however, depend on the type of reactor or reactors employed. Otherwise, the process is generally run at atmospheric pressure.

As discussed above, for process and safety reasons, the above-described mixed acid nitration wherein the N-alkyl phthalimide is first dissolved in concentrated sulfuric acid, and concentrated nitric acid is slowly added to the sulfuric acid solution can be preferred. In some embodiments, the nitric acid and the sulfuric acid can be premixed, and the combination can be contacted with the N-alkyl phthalimide. In some embodiments, the N-alkyl phthalimide, the nitric acid, and the sulfuric acid can be mixed simultaneously.

The N-alkyl nitrophthalimide product can be isolated from the product mixture by adding water to precipitate the N-alkyl nitrophthalimide product composition, and isolating the precipitate, for example by filtration or centrifugation. The isolated precipitate product is then washed with water. Washing can be accomplished using a belt filter, centrifuging, an agitated nutsche filter, or a combination comprising at least one of the foregoing. Washing with water removes the acids used in the nitration process and the more water-soluble 4-hydroxy-3,5-dinitro-N—($C_{1-13}$ alkyl)phthalimide, specifically the DNPI. Washing is conducted for a time effective to remove the 4-hydroxy-3,5-dinitro-N—($C_{1-13}$ alkyl)phthalimide to the desired extent. However, although the 3- and 4-nitro-N—($C_{1-13}$ alkyl)phthalimides are less soluble in water, extended washing to remove the 4-hydroxy-3,5-dinitro-N—($C_{1-13}$ alkyl)phthalimide can result in an overall lower yield. Washing the isolated precipitated product mixture with water can provide an N-alkyl nitrophthalimide composition comprising 4-nitro-N—($C_{1-13}$ alkyl)phthalimide, 1-10000 ppm, 1-7000 ppm, or 1-6000 ppm of 4-hydroxy-3,5-dinitro-N—($C_{1-13}$ alkyl)phthalimide, and 0-5 wt %, or 0.1-3.5 wt %, or 1-2 wt % of 3-nitro-N—($C_{1-13}$ alkyl)phthalimide. The washed product mixture can be in the form of a "wet cake" having a solids content of, for example, 10-90 wt %, or 40 to 80% by weight, and can optionally be further diluted with water to form an aqueous suspension or slurry for further processing, for example to 10-50 wt %.

In some embodiments, the process further comprises contacting the washed product mixture with an aqueous alkali metal carbonate or aqueous alkali metal hydrogen carbonate solution, followed by extraction of the 4-nitro-N—($C_{1-13}$ alkyl)phthalimide into a solvent, for example as described in U.S. Pat. No. 8,080,671. Contacting the washed product mixture is effective to remove residual acid from the product mixture. Contacting the washed product mixture can be by adding the alkali metal carbonate or alkali metal hydrogen carbonate to the precipitated product mixture as a solid or as a solution, to obtain the desired solids content. It is also possible to add any amount of desired additional water at any point in the process. For example, a higher solids wet cake can be diluted with water to form a slurry, and the alkali metal carbonate or alkali metal hydrogen carbonate can be added directly to the slurry to provide the aqueous solution of the alkali metal carbonate or alkali metal hydrogen carbonate. In some embodiments, the aqueous alkali metal carbonate comprises sodium carbonate or sodium hydrogen carbonate, preferably sodium hydrogen carbonate.

After the precipitated product mixture is contacted with the aqueous alkali metal carbonate or aqueous alkali metal hydrogen carbonate solution, an organic solvent is added, for example, toluene, benzene, xylene, chlorobenzene, anisole, or a combination comprising at least one of the foregoing, to form a two-phase mixture. The two-phase mixture can be heated, for example to 50-100° C. to effect dissolution of the 4-nitro-N—($C_{1-13}$ alkyl)phthalimide into the organic solvent, thus providing the N-alkyl nitrophthalimide composition. The two-phase mixture can be separated to provide an aqueous phase and an organic phase, wherein the aqueous phase contains the more water-soluble 4-hydroxy-3,5-dinitro-N—($C_{1-13}$ alkyl)phthalimide, specifically the DNPI, and the organic phase comprises the N-alkyl nitrophthalimide composition. The amount of the alkali metal carbonate or alkali metal hydrogen carbonate, the temperature of the dissolution and extraction, and the time for extraction are adjusted to separate the 4-hydroxy-3,5-dinitro-N—($C_{1-13}$ alkyl)phthalimide to the desired extent, without decreasing yield of the 3- and 4-nitro-N—($C_{1-13}$ alkyl)phthalimides, which have some water solubility. In some embodiments, the organic phase can include the 4-nitro-N—($C_{1-13}$ alkyl)phthalimide, 1-10000 ppm, 1-7000 ppm or 1-6000 ppm of 4-hydroxy-3,5-dinitro-N—($C_{1-13}$ alkyl) phthalimide, and 0.001-5 wt %, or 0.1-3.5 wt %, or 2-3 wt % of 3-nitro-N—($C_{1-13}$ alkyl)phthalimide, each based on the amount of the 4-nitro-N—($C_{1-13}$ alkyl)phthalimide.

It is also possible to contacting the washed product mixture with the organic solvent, with optional heating to effect dissolution of the 4-nitro-N—($C_{1-13}$ alkyl)phthalimide into the organic solvent and form two phases. The alkali metal carbonate or alkali metal hydrogen carbonate can then be added, as a solid or as a solution, the phases mixed, and then separated to provide a purified 4-nitro-N—($C_{1-13}$ alkyl)

phthalimide composition in the organic phase, which can contain 1-10000 ppm, 1-7000 ppm or 1-6000 ppm of 4-hydroxy-3,5-dinitro-N—($C_{1-13}$ alkyl)phthalimide, and 0.001-5 wt %, or 0.1-3.5 wt %, or 2-3 wt % of 3-nitro-N—($C_{1-13}$ alkyl)phthalimide, each based on the amount of the 4-nitro-N—($C_{1-13}$ alkyl)phthalimide In still another embodiment, the washed N-alkyl nitrophthalimide product mixture is optionally first diluted with water, and then contacted with an organic solvent immiscible with water at elevated temperature, as described above, to provide a two-phase mixture. The two phases are separated, to result in the organic solvent phase containing the purified 4-nitro-N—($C_{1-13}$ alkyl)phthalimide composition. Or, optionally, after being separated from the water phase, the organic solvent phase can be further contacted with an aqueous alkali metal carbonate solution or an aqueous alkali metal hydrogen carbonate solution. Again, the amount of the alkali metal carbonate or alkali metal hydrogen carbonate, the temperature of the dissolution and extraction, and the time for extraction are adjusted to separate the 4-hydroxy-3,5-dinitro-N—($C_{1-13}$ alkyl)phthalimide to the desired extent, without decreasing yield of the 3- and 4-nitro-N—($C_{1-13}$ alkyl)phthalimides, which have some water solubility. The organic phase can include the 4-nitro-N—($C_{1-13}$ alkyl) phthalimide, 1-10000 ppm, 1-7000 ppm or 1-6000 ppm of 4-hydroxy-3,5-dinitro-N—($C_{1-13}$ alkyl)phthalimide, and 0-5 wt %, or 0.1-3.5 wt %, or 2-3 wt % of 3-nitro-N—($C_{1-13}$ alkyl)phthalimide, each based on the amount of the 4-nitro-N—($C_{1-13}$ alkyl)phthalimide.

In any of the foregoing embodiments, the 4-hydroxy-3,5-dinitro-N—($C_{1-13}$ alkyl)phthalimide can be present in the washed or purified compositions in an amount of 1-10000, 1-7000 ppm, or 1-6000 ppm, or 1-5000 ppm, or 1-4000 ppm, or 1-3000 ppm, or 500-7000 ppm, 500-6000 ppm, or 500-5000 ppm, or 500-4000 ppm, or 500-3000 ppm, or 1000-7000 ppm or 1000-6000 ppm, or 1000-5000 ppm or 1000-4000 ppm, or 1000-3000, and 0.001-5 wt %, or 0.1 to 3.5 wt. %, or 1-2 wt % of 3-nitro-N—($C_{1-13}$ alkyl)phthalimide, each based on the total weight of the isolated or isolated and purified N-alkyl nitrophthalimide composition.

In some embodiments, the purified N-alkyl nitrophthalimide compositions comprise 1-6000 ppm, or 1-5000 ppm, or 1-4000 ppm, or 500-3000 ppm, or 1000-3000 ppm, or 100-500 ppm, or 1-1000 ppm, or 50-1000 ppm of 4-hydroxy-3,5-dinitro-N—($C_{1-13}$ alkyl)phthalimide and 1-2 wt % of 3-nitro-N—($C_{1-13}$ alkyl)phthalimide.

The invention is further described by the following non-limiting Examples.

EXAMPLES

The following abbreviations are used in these Examples.

| | |
|---|---|
| 4NPI | 4-Nitro-N-methyl phthalimide |
| 3NPI | 3-Nitro-N-methyl phthalimide |
| "SABIC" 4NPI | 4NPI made by the all-nitric process; contains no significant amount of DNPI |
| "Source 1" 4NPI | 4NPI made by a mixed acid process, contains 200-20000 ppm of DNPI |
| DNPI | 3,5-Dinitro-4-hydroxy-N-methyl phthalimide |
| BPANa$_2$ | Bisphenol A disodium salt |
| HEGCl | Hexaethylguanidinium chloride |
| C6B | Bis(tri-n-butylammonium)-1,6-hexane dibromide |
| TBAB | tetrabutylammonium bromide |
| YI | Yellowness index |
| NM | Not measured |
| NA | Not applicable |
| BPA bisimide | Bis(N-methylphthalimide) of bisphenol A |

Method 1A. Preparation of 4NPI for Use in Bisimide Manufacture

A 4-N-methylphthalimide/water wet cake (50.0 grams (g) dry weight, containing 10-60% water), resulting from either a mixed acid (H$_2$SO$_4$/HNO$_3$) nitration of N-methylphthalimide or an all nitric acid nitration of N-methylphthalimide, was charged to a 1000 mL, single-necked (24/40 joint) round-bottomed flask, equipped with a magnetic stir bar, and means to heat the flask with an external temperature controlled oil bath. The flask was then charged with 367 g of toluene, and enough additional deionized water was added such that the total amount of water present in the flask was equal to 160 g. The amount of water used targeted 20 to 25 wt % of 4NPI with respect to the total weight of 4NPI and water. The reaction mixture was magnetically stirred with an oil bath set temperature of 90° C. After the 4NPI had dissolved in the toluene the stirring was stopped, and the lower water phase was removed via pipette. This method of dissolution and separation of the 4NPI toluene phase from the aqueous phase constitutes a purification of the 4NPI as water soluble impurities were extracted from the 4NPI/toluene phase into the aqueous phase. This dissolution/separation method is termed herein the "4NPI Extraction." The 4NPI toluene solution was then placed on a rotoevaporator, equipped with a hot oil bath to heat the flask, and plumbed to a cold trap connected to a vacuum pump. The flask was rotated in the hot oil bath (temperature controlled at 110° C.) and the solvent was removed under reduced pressure (<30 mm). Once the majority of toluene had been removed, the flask was allowed to rotate in the oil bath at 110° C., 25 mm, for 60 minutes, to afford a dry solid free of toluene and water. The solid was transferred to a glove box inerted with dry nitrogen. The desired dried catalyst (HEGCl, TBAB, or C6B) was added to the dried 4NPI for the bisimide forming reaction.

Method 1B. Preparation of 4NPI/Catalyst for Use in Bisimide Manufacture: Dissolution in Toluene, Separation of Phases, Drying Solid Catalyst with 4NPI/Toluene Phase.

This method is substantially the same as Method 1A except that after the water was removed from the organic phase, the desired amount of pure phase transfer catalyst (HEGCl, TBAB, or C6B) for the reaction between 4NPI and BPANa$_2$ was added to the toluene solution of 4NPI. The toluene was then removed as described in Method 1A to afford a dry solid of 4NPI containing the phase transfer catalyst.

Method 1C. Preparation of 4NPI/Catalyst for Use in Bisimide Manufacture: Dissolution in Toluene, Separation of Phases, Drying Brine Solution of HEGCl with 4NPI/Toluene Phase.

This method is substantially the same as Method 1A except that after the water was removed from the organic phase, the desired amount of HEGCl (dissolved in an aqueous sodium chloride solution) for the reaction between 4NPI and BPANa$_2$ was added to the toluene solution of 4NPI. The toluene was then removed as described in Method 1A to afford a dry solid of 4NPI containing the HEGCl/NaCl.

Method 1D. Preparation of 4NPI for Use in Bisimide Manufacture: Dissolution in Toluene, Removal of Water and Toluene Under Vacuum.

The appropriate amount of 4NPI wet cake, containing 0.1-60% water, was dissolved in toluene at 85° C., under nitrogen, with stirring, in a 1-liter single-necked, round-bottomed flask, at 12 wt % solids (12 wt % 4NPI in the toluene employed). The two phase mixture (aqueous phase and 4NPI/toluene phase) was then placed on a roto-evaporator, equipped with a hot oil bath to heat the flask, and plumbed to a cold trap connected to a vacuum pump. The flask was rotated in the hot oil bath (temperature controlled at 110° C.) and the solvent and water was removed under reduced pressure (<30 mm). Once the majority of toluene and water had been removed, the flask was allowed to rotate in the oil bath at 110° C., 25 mm, for 60 minutes, to afford a dry solid free of toluene and water. The solid was transferred to a glove box inerted with dry nitrogen. This procedure did not employ the 4NPI Extraction.

Method 1E. Preparation of Dried HEGCl/NaCl

A 2-liter, single-necked, round-bottomed flask was charged with 100 g of an aqueous solution containing 30.0 g of HEGCl and 14 g of sodium chloride, and 800 mL of toluene. The mixture was then placed on a roto-evaporator, equipped with a hot oil bath to heat the flask, and plumbed to a cold trap connected to a vacuum pump. The flask was rotated in the hot oil bath (temperature controlled at 110° C.) and the solvent was removed under reduced pressure (<30 mm). Once the majority of the toluene/water had been removed, the flask was allowed to rotate in the oil bath at 130° C., 25 mm, for 60 minutes, to afford a dry solid HEGCl/NaCl, free of toluene and water. The solid was transferred to a glove box inerted with dry nitrogen.

Method 2. Preparation of BPANA$_2$ as a Toluene Slurry for Use in Bisimide Manufacture (Total Isolation Method)

A 3-necked, 2-liter round-bottomed flask, equipped with a Dean and Stark receiver topped with a water cooled or glycol cooled reflux condenser, a mechanical stirrer, and a means for maintaining a nitrogen atmosphere, was charged with 114.15 g (0.5 moles (mol)) of bisphenol A and 450 mL of degassed deionized (DI) water. A commercial ampoule of 1.0N NaOH (from JT Baker) was then added to the vessel. The ampoule was rinsed with 50 Ml of degassed DI water into the vessel. Caution was taken to keep the material under an inert nitrogen atmosphere.

The vessel was then heated with stirring using a temperature controlled external oil bath, to 95° C. under nitrogen. The BPA reacted with the caustic to provide a clear near-colorless solution of BPA disodium salt in water. One liter of degassed reagent grade toluene was added to the vessel.

The oil bath temperature was raised to 150° C., and the water-toluene azeotrope was condensed overhead. Water was withdrawn from the Dean and Stark receiver so that water was not allowed to spill back into the reactor. Toluene in the Dean and Stark receiver was allowed to drain back into the reactor. BPANa$_2$ precipitated as the water was removed from the flask. The distillation process was allowed to continue until all the bulk water was removed from the flask. Caking of BPA salt on the sides of the flask was typically observed.

Approximately 500 mL of dry degassed toluene (containing <10 ppm water) was then added to the vessel and then 500 mL of toluene was boiled off from the vessel with the use of the external oil bath set at 150° C., and collected from the Dean and Stark receiver in an external vessel. This was repeated twice more to afford a finally divided white slurry of BPANa$_2$ in toluene at 12-15 weight percent solids (wt. % s). Additional aliquots (200 mL each) of dry toluene were added to the flask and removed sequentially by distillation until the moisture of the condensed toluene from the Dean and Stark receiver contained <20 ppm of water as determined by Karl Fischer Titration. The slurry was allowed to cool to room temperature under nitrogen. The slurry was assayed via titration against 1N HCL to determine the wt. % s of BPANa$_2$ in the slurry. The slurry was stored under nitrogen to avoid degradation and the adsorption of water.

Method 3. Preparation of Dry Solid BPANa$_2$ for Use in Bisimide Manufacture

The BPANa$_2$/toluene product of Method 2 or Method 4 was placed on a roto-evaporator, equipped with a hot oil bath to heat the flask, and plumbed to a cold trap connected to a vacuum pump. The flask was rotated in the hot oil bath (temperature controlled at 150° C.) and the solvent was removed under reduced pressure (<30 mm) to afford a dry white solid of BPANa$_2$ free of toluene. The cake was transferred to a glove box inerted with dry nitrogen.

Method 4. Preparation of BPANa$_2$ as a Toluene Slurry for Use in Bisimide Manufacture (Continuous Addition of Aqueous Salt to Refluxing Toluene)

Aqueous BPA disodium salt was prepared as described in Method 2, only at about 10 wt. % s under nitrogen. This concentration of salt remains in solution at room temperature. The salt reactor described in Method 1 was again utilized (i.e., a 2-liter, 3-necked round-bottomed flask, equipped with a Dean and Stark receiver topped with a reflux condenser, a mechanical stirrer, means for maintaining a nitrogen atmosphere, and an external oil bath).

The flask was charged with 1 liter of reagent grade toluene and brought to reflux (130-150° C. oil temperature) under nitrogen. The aqueous salt under nitrogen was then delivered to the flask with the use of a peristaltic pump using Viton tubing with the appropriate adapter to the flask. The aqueous salt was delivered at a rate at which the azeotrope distills from the reactor (also known as the drier) in a controlled manner, typically around 3 mL/min. The BPANa$_2$ precipitated immediately upon addition. Caking of salt in the vessel occurred to a lesser extent using this method than Method 2.

The water was continuously removed from the collection arm of the Dean and Stark receiver as the aqueous salt was pumped into the vessel. Once the aqueous solution had been completely delivered to the drying vessel, dry toluene (<10 ppm water) was then pumped into the reactor at reflux, and toluene was continuously distilled overhead and continuously drained from the receiver and not allowed to drain back to the vessel. The level in the vessel was held constant during this process. Distillation of between 500 to 1000 mL of toluene resulted in a condensed toluene moisture content of <20 ppm and finely divided solid BPANa$_2$ suspended in toluene remaining in the vessel at ~12 wt. % s. The toluene from the slurry can be distilled overhead to achieve the desired wt. % s in the vessel. The slurry was allowed to cool to room temperature under nitrogen. The slurry was assayed via titration against 1N HCL to determine the wt. % s of BPANa$_2$ in the slurry. The slurry was stored under nitrogen to avoid degradation and the adsorption of water.

Method 5A. Synthesis of Bisimide.

A 250-mL, 3-necked, round-bottomed flask with 24/40 female joints, was placed in a glove box under nitrogen. The flask was charged with 50 g of a 15.0 wt. % s BPANa$_2$ toluene slurry (7.5 g BPANa$_2$, 0.0275 mol) and 50 mL of dry toluene (<10 ppm water content). The necks were then fitted with stoppers. A glass tube, wherein one end had a 24/40 male joint and the other end a stopcock, 15 mm internal diameter and 180 mm in length, was charged in a glove box inerted with nitrogen with 11.36 g (0.551 mol) of 4NPI prepared as in Method 1A, 1B, 1C, or 1D. The tube was charged with the desired amount of pure DNPI. The tube was also charged with the desired amount of dry solid HEGCl catalyst (at 1 mol %, 73 mg, with respect to the dry weight of BPANa$_2$ employed; or 2 mol %, 146 mg). The catalyst charged was either dry crystalline HEGCl, dried HEGCl/NaCl prepared as in Method 1E, dried TBAB, or dried C6B. The tube was then capped with a 24/40 female glass cap. If the catalyst had been dried with the 4NPI, then the dried 4NPI containing the catalyst was charged to the tube.

The flask containing the BPANa$_2$ toluene slurry was moved to a ventilated hood and equipped with a magnetic stir bar, and a Dean and Stark receiver topped with a reflux condenser, and means for maintaining a nitrogen atmosphere. One neck of the flask was fitted with a Teflon® stopper, the other neck was fitted with a controlled nitrogen supply. The flask was heated with an external oil bath controlled at a temperature of 130° C. The oil bath was dropped from the flask to stop the toluene reflux. The tube containing the 4NPI and catalyst was removed from the dry box, the cap removed, the stopper on the vessel containing the salt was removed, and the male fitting on the tube was rapidly inserted into the neck of the vessel. The contents of the tube were dropped into the flask containing the salt slurry. The oil bath was raised to again heat the flask (oil bath temperature set point of 130° C.). A slow stream of nitrogen was established at the neck of the flask, and then the stopcock on the now vertical tube was opened. The toluene refluxed up the tube, condensed in the tube, washing all the 4NPI and catalyst down into the flask. Once the tube was clean, the tube was removed and the neck was plugged with a 24/40 stopper.

Dried solid BPANa$_2$ salt, prepared by Method 3 can also be used in this procedure. The desired amount of salt was weighed into the reaction vessel in an inert atmosphere glove box with nitrogen. The desired amount of dry toluene (<10 ppm water) was then added to the vessel, and this mixture was then reacted with 4NPI as described above.

Over the first 15 minutes of the reaction, 25 and 50 mL of toluene were removed by distillation through the Dean and Stark receiver. The reaction was exothermic and was allowed to proceed with stirring under nitrogen with an oil bath temperature of 130° C. for 90 minutes. The reaction mixture was then cooled to 83° C. with the use of the temperature controlled oil bath. The reaction mixture was sampled to determine the yield of bisimide by High Pressure Liquid Chromatography.

The reaction mixture was then magnetically stirred with 10 g of 1 wt. % sodium hydroxide at 80-84° C. under nitrogen for 5 minutes. The stirring was stopped, and the phases were allowed to separate. The lower aqueous phase was removed via pipette. The clear organic phase was washed twice more in the same manner to afford a clear toluene solution of BPA bisimide at ~23 wt. % s. The solution was transferred to a clean 1-necked, 250-mL, round-bottomed flask and was placed on a roto-evaporator, equipped with a hot oil bath to heat the flask, and plumbed to a cold trap connected to a vacuum pump. The flask was rotated in the hot oil bath (temperature controlled at 180° C.) and the solvent was removed under reduced pressure (<30 mm) to afford purified BPA bisimide. The material was allowed to cool and solidify. The Yellowness Index (YI) of the BPA bisimide was measured with a Macbeth 7000 spectrometer using ASTM D-1925. A blank of methylene chloride was measured for YI prior to measurement of the sample. This YI blank measurement was recorded for use in correcting the final measurement. About 0.5 g of a sample of the solid BPA bisimide was dissolved in 10 mL of methylene chloride. The sample was then filtered through a 0.5 micrometer filter. The solution was then transferred to a 3.7 cm×5 cm×10 mm path length glass cell. The cell was placed into the colorimeter and the YI was determined.

Method 5B. Synthesis of BPA Bisimide.

A 250-mL, 2-necked, round-bottomed flask with 24/40 female joints, was placed in a glove box under nitrogen. The flask was charged with 50 g of a 15.0 wt. % s BPANa$_2$ dry toluene slurry (7.5 g BPANa$_2$, 0.0275 mol). The flask was then fitted with rubber sleeve stoppers that were folded over the necks of the joints. The stoppers permitted the insertion of a needle cannula or a needle pressurized nitrogen supply.

A 250-mL, 3-necked, round-bottomed flask with 24/40 female joints, was placed in a glove box under nitrogen and charged with dried 4NPI (11.36 g, 0.0551 mol). The 4NPI used may have already contained the desired amount of phase transfer catalyst. If not, the desired amount of dry catalyst was also added to the vessel. The vessel was then charged with 50 mL of dry toluene containing <10 ppm water. The vessel was stopped (one of the stoppers was a rubber sleeve folded over the neck) and transferred to a ventilated hood and equipped with a magnetic stir bar, a Dean and Stark Receiver topped with a reflux condenser, and means for maintaining a nitrogen atmosphere. The vessel was heated with a temperature controlled oil bath. The flask containing the BPANa$_2$ salt toluene slurry was then transferred to the ventilated hood.

The vessel containing the 4NPI/catalyst/toluene was heated (oil temperature of 130° C.). One end of a cannula needle on both ends was inserted into the rubber sleeve on the vessel containing the 4NPI and the other end was inserted through the rubber sleeve on the flask containing the BPANa$_2$ salt slurry wherein the end of the cannula rested on the bottom of the flask. A needle regulated nitrogen supply was inserted into the other rubber sleeve on the flask containing the salt slurry. Nitrogen pressure was carefully applied to the vessel containing the salt slurry and the slurry was transferred to the vessel containing the 4NPI/catalyst/toluene mixture. Once the transfer was complete, the cannula was removed from both flasks. Over the first 15 minutes of the reaction, 25 and 50 mL of toluene was removed by distillation through the Dean and Stark receiver. The reaction was exothermic and was allowed to proceed with stirring under nitrogen with an oil bath temperature of 130° C. for 90 minutes. The reaction mixture was then cooled to 83° C. with the use of the temperature controlled oil bath. The reaction mixture was sampled to determine the yield of BPA bisimide by High Pressure Liquid Chromatography. The rest of the procedure was the same as for Method 5A.

The following notes apply to the Tables shown below. The amount of DNPI present is with respect to the weight of 4NPI utilized in the bisimide forming reaction. All 4NPI used in the examples, unless otherwise noted, was first dissolved in toluene at elevated temperature in the presence of water. The toluene phase (containing the 4NPI) was then separated from the aqueous phase, and the toluene was removed to afford dry 4NPI. The dry 4NPI is referred to as "after 4NPI extraction." "DNPI Spike" refers to the amount of DNPI added to the 4NPI used in the reaction.

Examples 1-17. Effect of DNPI on Bisimide Yield at 2 Mole % Catalyst Loading

Table 1 shows the results of BPA bisimide forming reactions using 2 mole % catalyst (with respect to moles of disodium salt employed) with 4NPI containing various levels of DNPI.

TABLE 1

Bisimide Forming Examples 1-17.

| Ex. No. | 4NPI Source, Drying Method | DNPI in Starting 4NPI | DNPI After 4NPI Extraction | DNPI Spike | Catalyst | Mo % Catalyst | Salt Preparation Method | BPA-BI Forming Reaction Method | % Yield BI | BPA-BI YI |
|---|---|---|---|---|---|---|---|---|---|---|
| 1 | SABIC, Method 1A | <1 ppm | <1 ppm | None | HEGCl | 2 | Method 3 | Method 5A | 98.92 | 3.6 |
| 2 | SABIC, Method 1A | <1 ppm | <1 ppm | 2000 | HEGCl | 2 | Method 3 | Method 5A | 98.32 | 6.9 |
| 3 | SABIC, Method 1A | <1 ppm | <1 ppm | 2000 | C6B | 2 | Method 3 | Method 5A | 98.79 | 7.1 |
| 4 | SABIC, Method 1A | <1 ppm | <1 ppm | 2236 | HEGCl | 2 | Method 4 | Method 5B | 98.06 | 7.1 |
| 5 | SABIC, Method 1A | <1 ppm | <1 ppm | 2176 | C6B | 2 | Method 4 | Method 5B | 97.98 | 6.8 |
| 6 | SABIC, Method 1A | <1 ppm | <1 ppm | 3554 | HEGCl | 2 | Method 3 | Method 5A | 98.52 | 15.2 |
| 7 | SABIC, Method 1A | <1 ppm | <1 ppm | none | HEGCl | 2 | Method 3 | Method 5A | 99.49 | 3.3 |
| 8 | SABIC, Method 1A | <1 ppm | <1 ppm | 3889 | TBAB | 2 | Method 3 | Method 5A | 62.15 | 9.6 |
| 9 | SABIC, Method 1A | <1 ppm | <1 ppm | 3145 | HEGCl | 2 | Method 3 | Method 5A | 98.11 | 8.9 |
| 10 | SABIC, Method 1A | <1 ppm | <1 ppm | 4071 | HEGCl | 2 | Method 3 | Method 5A | 98.04 | 14.9 |
| 11 | SABIC, Method 1A | <1 ppm | <1 ppm | 6065 | HEGCl | 2 | Method 3 | Method 5A | 97.73 | 54.9 |
| 12 | SABIC, Method 1A | <1 ppm | <1 ppm | 11800 | HEGCl | 2 | Method 3 | Method 5A | 10.32 | NM |
| 13 | SABIC, Method 1A | <1 ppm | <1 ppm | none | HEGCl | 2 | Method 3 | Method 5A | 98.11 | 2.7 |
| 14 | Source 1, Method 1A | NM | 6400 | none | HEGCl | 2 | Method 3 | Method 5A | 93.32 | 10.6 |
| 15 | Source 1, Method 1A | NM | 5000 | none | HEGCl | 2 | Method 3 | Method 5A | 94.44 | 16.8 |
| 16 | Source 1, Method 1A | NM | 5400 | none | HEGCl | 2 | Method 3 | Method 5A | 95.76 | 22.1 |
| 17 | Source 1, Method 1A | 4400 | 4500 | none | HEGCl | 2 | Method 3 | Method 5A | 92.56 | 20.8 |

"SABIC" 4NPI is derived from the all nitric process, whereas "Source 1" 4NPI is derived from a mixed acid process. SABIC 4NPI does not contain any significant amount of DNPI. Reactions were spiked with purified DNPI when using SABIC 4NPI. The amount spiked was with respect to the weight of 4NPI used in the reaction.

Examples 1-7, 9-10, and 13 show that good yields (greater than 98%) of BPA bisimide with reasonably low color (YI less than about 15) can be obtained when using SABIC 4NPI with up to 4071 ppm of spiked DNPI, using either HEGCl or C6B as the catalyst. Example 11 shows that a reasonable yield (about 97.7%) of BPA bisimide can be obtained with very poor color (YI greater than 50) using SABIC 4NPI containing spiked with 6065 ppm of DNPI. Example 12 shows that using SABIC 4NPI spiked with 11800 ppm of DNPI results in a very poor yield (about 10%) of BPA bisimide. Example 8 shows that the use of TBAB at 2 mole % resulted in a poor yield of BPA bisimide (62.1%) when the SABIC 4NPI was spike with 3889 ppm of DNPI.

Examples 14-17 used 4NPI derived from the mixed acid process and contained DNPI. Reasonable yields (greater than 92%) of BPA bisimide could be obtained using 2 mole % of HEGCl under dry conditions, though the BPA bisimide color was elevated (YI >10, or even >20). The desired color of BPA bisimide is a YI of <5.

Examples 18-36. Effect of DNPI on BPA Bisimide Yield at 1 and 2 Mol % Catalyst Loading Examples 18-23 (Table 2) show that BPA bisimide can be prepared by Method 5A using SABIC 4NPI containing <1 ppm to ~1000 ppm of spiked DNPI, in the presence of 1 mol % HEGCl (with respect to the moles of BPANa$_2$ employed) in a yield >98.4% with a purified BPA bisimide of YI approximately 4-8.

TABLE 2

Bisimide Forming Examples 18-36.

| Ex. No. | 4NPI Source, Drying Method | DNPI in starting 4NPI | DNPI after 4NPI Extraction | DNPI Spike (ppm) | HEGCl Catalyst Level (Mol %) | Salt Preparation method | Displacement Method | BI Yield | BI YI |
|---|---|---|---|---|---|---|---|---|---|
| 18 | SABIC, Method 1A | <1 ppm | <1 ppm | none | 1% | Method 3 | Method 5A | 99.27 | 4.5 |
| 19 | SABIC, Method 1A | <1 ppm | <1 ppm | none | 1% | Method 3 | Method 5A | 98.97 | 3.8 |
| 20 | SABIC, Method 1A | <1 ppm | <1 ppm | 515 | 1% | Method 3 | Method 5A | 99.06 | 6.9 |
| 21 | SABIC, Method 1A | <1 ppm | <1 ppm | 512 | 1% | Method 3 | Method 5A | 98.42 | 4.9 |
| 22 | SABIC, Method 1A | <1 ppm | <1 ppm | 997 | 1% | Method 3 | Method 5A | 98.81 | 7.7 |
| 23 | SABIC, Method 1A | <1 ppm | <1 ppm | 951 | 1% | Method 3 | Method 5A | 98.97 | 8.7 |
| 24 | SABIC, Method 1A | <1 ppm | <1 ppm | 2042 | 1% | Method 3 | Method 5A | 76.07 | 8.5 |
| 25 | SABIC, Method 1A | <1 ppm | <1 ppm | 2016 | 1% | Method 3 | Method 5A | 61.81 | 8 |
| 26 | SABIC, Method 1A | <1 ppm | <1 ppm | 1972 | 1% | Method 3 | Method 5A | 77.28 | 7.1 |
| 27 | SABIC, Method 1A | <1 ppm | <1 ppm | 2051 | 2% | Method 3 | Method 5A | 98.78 | 5.2 |
| 28 | SABIC, Method 1A | <1 ppm | <1 ppm | none | 2% | Method 3 | Method 5A | 99.23 | 3.9 |
| 29 | SABIC, Method 1A | <1 ppm | <1 ppm | none | 2% | Method 3 | Method 5A | 99.19 | 3.6 |
| 30 | SABIC, Method 1A | <1 ppm | <1 ppm | 2025 | 2% | Method 3 | Method 5A | 98.88 | 3.9 |
| 31 | SABIC, Method 1A | <1 ppm | <1 ppm | 555 | 2% | Method 3 | Method 5A | 98.99 | 3.5 |
| 32 | SABIC, Method 1A | <1 ppm | <1 ppm | 563 | 2% | Method 3 | Method 5A | 99.2 | 3.1 |
| 33 | SABIC, Method 1A | <1 ppm | <1 ppm | 992 | 2% | Method 3 | Method 5A | 99.14 | 4.1 |
| 34 | SABIC, Method 1A | <1 ppm | <1 ppm | 1020 | 2% | Method 3 | Method 5A | 98.96 | 3.6 |
| 35 | SABIC, Method 1A | <1 ppm | <1 ppm | 3034 | 2% | Method 3 | Method 5A | 98.77 | 4.6 |
| 36 | SABIC, Method 1A | <1 ppm | <1 ppm | 1974 | 2% | Method 4 | Method 5A | 99.29 | 3 |

Examples 24-26 show that bisimide yield drops to ~60% to ~77% under the same conditions when the SABIC 4NPI contains approximately 2000 ppm of spiked DNPI. Additionally, the BPA bisimide YI is consistently higher than in examples 19-23 (YI 8 vs YI 4-8). Examples 27-36 show that BPA bisimide can be prepared by Method 5A using SABIC 4NPI containing <1 ppm to ~3000 ppm of spiked DNPI when 2 mol % catalyst is employed in the BPA bisimide forming reaction. The BPA bisimide produced in examples 27-36 had a YI of 3-5, an improvement over examples 20-26 (BPA bisimide YI 5-8.7).

Examples 37-41. Effect of DNPI on BPA Bisimide Yield Using 1 Mole % Catalyst

The effect of DNPI on the BPA bisimide yield was studied in examples 37-41 using only 1 mole % HEGCl catalyst. SABIC 4NPI was spiked with 2120-4060 ppm of DNPI and used in the bisimide forming reaction. The desired yield of 4NPI is >99%. Anything lower impacts productivity of a manufacturing process. The BPA bisimide yield was >99% when 2120 ppm of DNPI was present in the 4NPI (Table 3). However, the BPA bisimide yield dropped to 96% when 2508 ppm was present in the 4NPI. At 4060 ppm DNPI in the 4NPI, the BPA bisimide yield was only 16.59%.

TABLE 3

Bisimide Forming Examples 37-41.

| Ex. No. | 4NPI Source, Drying Method | DNPI in starting 4NPI (ppm) | DNPI spike | Catalyst | Mol % Catalyst (wrt moles of $BPANa_2$) | Salt Preparation Method | BI Forming Reaction Method | BI yield |
|---|---|---|---|---|---|---|---|---|
| 37 | SABIC, Method 1A | <1 | 2120 | HEGCL | 1% | Method 3 | Method 5A | 99.32 |
| 38 | SABIC, Method 1A | <1 | 2508 | HEGCL | 1% | Method 3 | Method 5A | 96.09 |
| 39 | SABIC, Method 1A | <1 | 3004 | HEGCL | 1% | Method 3 | Method 5A | 62.93 |
| 40 | SABIC, Method 1A | <1 | 3180 | HEGCL | 1% | Method 3 | Method 5A | 81.22 |
| 41 | SABIC, Method 1A | <1 | 4060 | HEGCL | 1% | Method 3 | Method 5A | 16.59 |

Examples 42-50

Three samples of 4NPI resulting from the mixed acid nitration of N-methylphthalimide (PI) were used in BPA bisimide forming reactions, Table 4.

TABLE 4

Bisimide Forming Reactions with 4NPI Derived from Mixed Acid Nitration.

| Ex. No. | 4-NPI source Drying Method | DNPI in Starting 4NPI Extraction | DNPI after 4NPI Extraction | DNPI Spike (ppm wrt wt 4NPI) | HEGCl Level (mol % wrt mol of $BPANa_2$) | $BPANa_2$ Form | Displacement Method | BPA-BI Yield | YI |
|---|---|---|---|---|---|---|---|---|---|
| 42 | Mixed Acid Based NPI-1, Method 1D | 1750 | Extraction not done | none | 1% | slurry | 5A | <50 | NM |
| 43 | Mixed Acid Based NPI-1, Method 1A | 1750 | Extraction not done | none | 1% | slurry | 5A | 86.7 | 9 |
| 44 | Mixed Acid Based NPI-2, Method 1A | 1700 | 300 | none | 1% | slurry | 5A | 99.3 | 3.4 |
| 45 | Mixed Acid Based NPI-2, Method 1A | 1700 | 300 | none | 1% | slurry | 5A | 99.6 | 2.8 |
| 46 | Mixed Acid Based NPI-2, Method 1D | 1700 | Extraction not done | none | 2% | slurry | 5A | 82.5 | 12 |
| 47 | Mixed Acid Based NPI-3, Method 1D | 1300 | Extraction not done | none | 1% | slurry | 5A | 98.8 | 4.4 |
| 48 | Mixed Acid Based NPI-3, Method 1D | 1300 | Extraction not done | none | 1% | slurry | 5A | 99.6 | 3.4 |
| 49 | Mixed Acid Based NPI-3, Method 1A | 1300 | 120 | none | 1% | slurry | 5A | 99.2 | 3.2 |
| 50 | Mixed Acid Based NPI-3, Method 1A | 1300 | 120 | none | 1% | slurry | 5A | 99.2 | 2.5 |

The first sample (NPI-1) contained 1750 ppm of DNPI. This material when dried using Method 1D (there was no water extraction step) and used in the displacement forming reaction failed to give an acceptable yield of BPA bisimide, experiment 42. When this 4NPI was dried using Method 1A (with the water extraction step), and used in the BPA bisimide forming reaction, a better but still unacceptable yield of BPA bisimide was obtained (86.7% experiment 43). Impurities were present that were not removed in the water extraction step and subsequently resulted in a low yield of BPA bisimide. These other impurities were not identified.

Another sample of mixed acid derived 4NPI (4NPI-2) contained 1700 ppm of DNPI. When the material was dried by Method 1D, a 82.5% yield of BPA bisimide with a YI of 12 was obtained (experiment 46). However, when this material was dried using Method 1A, BPA bisimide was obtained in >99.3% yield with a YI of <3.5 (experiments 44 and 45). This showed the variable purity of mixed acid derived 4NPI and the impact on BPA bisimide yield even with the water extraction of the 4NPI prior to the BPA bisimide forming reaction.

Yet a different sample of mixed acid derived 4NPI (4NPI-3) was dried with and without the water extraction procedure of Method 1A. In both cases, good yields of bisimide (>99.2%) with good color (YI<3.5) were obtained (examples 47-49). Again this variable purity of mixed acid derived 4NPI and the impact of the product of the BPA bisimide forming reaction is not understood.

Examples 51-55. Purification of 4NPI with Sodium Bicarbonate

A method similar to Method 1A to purify 4NPI derived from mixed acid nitration containing impurities was desired that would afford purified 4NPI that when used in a bisimide forming reaction would provide a high yield of bisimide with low YI. The 4NPI used in these examples contained 17.4% water, 3800 ppm DNPI and 3.32 wt % 3NPI (with respect to the total weight of 3- and 4NPI), and was titrated with 0.1N NaOH to determine the amount of acid equivalents also present. The titration determined the moles of DNPI (a phenolic acid), moles of any residual sulfuric or nitric acid, as well as moles of carboxylic acids present in the 4NPI sample. It was found that a 48.29 g sample of the 4NPI wet cake contained 0.00345 moles of acid equivalents. This sample of 4NPI was purified as in Method 1A, except that varying amounts of sodium bicarbonate (0.5 to 2 equivalents of sodium bicarbonate with respect to the moles of acid present as determined by titration) were added to the mixture of 4NPI, water, and toluene.

Samples of this 4NPI wet cake (48.29 g, 82.6 wt % 4NPI with the balance being water, 40 g dry weight of 4NPI) were charged to a 1000-mL, 3-necked, round-bottomed flask equipped with a stir bar, a reflux condenser, and means to maintain a nitrogen atmosphere. The flask was then charged with 18.3 g of water, 293.3 g of toluene, and varying amounts of sodium bicarbonate, Table 5. The mixture was stirred and heated with an external temperature controlled oil bath with an oil set temperature of 90° C.

The 4NPI dissolved in the toluene after 15 minutes of heating at 90° C. The mixing was stopped and the phases were allowed to separate. The lower phase was drawn off the bottom of the vessel with a pipette. The pH of the aqueous phase was determined. The aqueous phase was charged to a 250-mL, 1-necked, round-bottomed flask. The water was removed on a rotary evaporator at reduced pressure (25 mm) with the use of an externally temperature controlled oil bath with an oil set temperature of 100° C., to afford a dry solid, which was weighed.

A portion of the 4NPI/toluene solution was then placed on a roto-evaporator, equipped with a hot oil bath to heat the flask, and plumbed to a cold trap connected to a vacuum pump. The flask was rotated in the hot oil bath (temperature controlled at 110° C.) and the solvent was removed under reduced pressure (<30 mm). Once the majority of toluene had been removed the flask was allowed to rotate in the oil bath at 110° C., 25 mm, for 60 minutes, to afford a dry solid free of toluene and water. The solid was then analyzed by HPLC, Table 5.

As can be seen in Table 5, the use of 1 equivalent of sodium bicarbonate (with respect to the moles of acid present in the 4NPI) removed all the DNPI without removing a significant amount of the 3NPI. Removal of the 3NPI is not desired as this material is used in the bisimide forming reaction. Use of the 4NPI treated with the 1 equivalent or greater resulted in high yield of bisimide.

TABLE 5

Purification of 4NPI with Sodium Bicarbonate and Impact on Bisimide Yield.

| Ex. No. | Mole equivalents of NaHCO3 added with respect to moles of acid present in 4NPI | NaHCO$_3$ Added (gr) | Wt % Solids of Aqueous Phase After Extraction | Wt % Solids of Organic Phase After 4NPI Extraction | Aqueous Phase pH | DNPI in Extracted 4NPI (ppm) | Wt % 3NPI in Extracted 4NPI | Bisimide % Yield |
|---|---|---|---|---|---|---|---|---|
| 51 | Control | 0 | 0.22 | 11.81 | 2.16 | 3100 | 3.32 | 96.2 |
| 52 | 0.5 equivalent | 0.1456 | 0.53 | 11.82 | 2.63 | 1400 | 3.07 | 99.2 |
| 53 | 1 equivalent | 0.2909 | 0.76 | 11.87 | 4.82 | 0 | 3.11 | 99.4 |
| 54 | 1.5 equivalents | 0.4348 | 1.01 | 11.60 | 5.50 | 0 | 3.02 | 99.3 |
| 55 | 2 equivalents | 0.5820 | 1.23 | 11.62 | 5.37 | 0 | 2.90 | 99.1 |

Example 56. Mixed Acid Nitration of N-Methylphthalimide to Produce 4NP

A 1-liter, 3-necked round-bottomed flask, located in a ventilated laboratory fume hood, equipped with a mechanical stirrer, a constant addition funnel, and a temperature indicator to monitor the temperature of the reaction mixture, was charged with 80.5 g (0.50 mol) of N-methylphthalimide and 188 g of 98% sulfuric acid. The mixture was stirred and heated with an external temperature controlled water bath to 30-35° C. to afford a solution of N-methylphthalimide in sulfuric acid. The constant addition funnel was open to the atmosphere so as not to allow any pressure build in the reaction vessel. The constant addition funnel was charged with 36.59 g of 99 wt % nitric acid (0.575 mol, 1.15 mole equivalents).

With stirring, the nitric acid was slowly added to the reaction vessel, while observing the temperature of the reaction mixture. The reaction mixture was exothermic and the temperature increased. The reaction mixture was a homogenous solution. The nitric acid was added at such a rate where the temperature of the reaction did not exceed 45-50° C. Nitric acid addition was stopped if no exotherm was observed. Ice was added to the water bath in the event that the temperature exceeded 45° C. and the addition of nitric acid was momentarily ceased. The nitric acid addition was reestablished once the reaction temperature was 40-45° C. The total time to add all the nitric acid was ~1 hour. The reaction mixture was allowed to stir at 40-50° C. for 2 hours, and the homogenous reaction solution was then cooled to room temperature with the use of an ice bath.

A 2-liter, 3-necked round-bottomed flask, located in a ventilated laboratory fume hood, equipped with a mechanical stirrer, a constant addition funnel, and a temperature indicator to monitor the temperature of the reaction mixture, was charged with 563.5 g of water. The constant addition funnel was charged with the nitration reaction mixture solution (~300 g). The flask was cooled with an external ice-water bath. The nitration reaction mixture was slowly added to the water and the product 4NPI precipitated from solution. The temperature of the diluted reaction mass was monitored and if the temperature exceeded 45° C. then the addition of the nitration reaction mixture to the vessel was ceased and ice was added to the water bath. The dilution of the entire nitration reaction mixture took on the order of 1 hour. The diluted mixture was allowed to cool to room temperature to afford a slurry of 4NPI in diluted sulfuric acid.

A 2-liter filter flask, placed in a ventilated laboratory hood, was fitted with a neoprene filter adapter. An appropriately sized porcelain Buchner funnel fitted with a 0.7 micrometer glass fiber filter (GF/F Whatman® brand filter paper) was placed on the adapter. The filter flask was plumbed to a Welch Dryfast® chemical duty vacuum pump. Vacuum was applied to the filter flask and the slurry was slowly poured into the filter as the mother liquor was suctioned from the Buchner funnel to afford a wet cake inside the Buchner funnel.

The cake was transferred to a 500-mL Erlenmeyer flask containing a magnetic stir bar. The flask was charged with 100 mL of water and the resulting slurry was stirred for 10 minutes and then vacuum filtered as described above. This procedure was repeated twice more to afford a 4NPI wet cake that was 40% water. The organic material present was 98.2 wt % 4NPI, 1.4 wt % 3NPI and 0.3 wt % DNPI, containing trace N-methylphthalimide and sulfuric acid (~1000 ppm).

The procedure to dilute the nitration reaction mixture with water can be modified to be a continuous process wherein water and reaction mixture are delivered in a controlled manner to a process capable of controlling the temperature to <45° C. The resulting slurry can be isolated using a continuous belt filter, an agitated nutsche filter, a centrifuge, or similar equipment. The precipitated product can be washed with water of varying temperature to afford a final wet cake where the solids include 97-99.9 wt % 4NPI, 0.01-2.5 wt % 3NPI, 500-10000 ppm DNPI, 100-1500 ppm sulfuric acid, and trace N-methylphthalimide; and a water content of of 5-50 wt %.

The compositions, methods, and articles are further illustrated by the following non-limiting embodiments.

Embodiment 1: A method for producing an aromatic bisimide, the method comprising reacting a dialkali metal salt of a dihydroxy aromatic compound with an N-alkyl nitrophthalimide composition under conditions effective to form a product mixture comprising the aromatic bisimide, wherein the N-alkyl nitrophthalimide composition comprises 4-nitro-N—($C_{1-13}$ alkyl)phthalimide, 3-nitro-N—($C_{1-13}$ alkyl)phthalimide, or a combination comprising at least one of the foregoing; and 4-hydroxy-3,5-dinitro-N—($C_{1-13}$ alkyl)phthalimide in an amount of 1-10000 ppm, or 50-10000 ppm, or 100-10000 ppm, or 500-10000 ppm, or 1000-10000 ppm; 1-8000 ppm, or 50-8000 ppm, or 100-8000 ppm, or 500-8000 ppm, or 1000-8000 ppm or 1-8000 ppm, or 50-8000 ppm, or 100-7000 ppm, or 500-7000 ppm, or 1000-7000 ppm; or 1-6000 ppm, or 50-6000 ppm, or 100-6000 ppm, or 500-6000 ppm, or 1000-6000 ppm; or 1-4000 ppm, or 50-4000 ppm, or 100-4000 ppm, or 500-4000 ppm, or 1000-4000 ppm; or 1-3000 ppm, or 50-3000 ppm, or 100-3000 ppm, or 500-3000 ppm, or 1000-3000; and wherein the aromatic bisimide is obtained in a yield of greater than 75%, or greater than 85%, or 9099.8%, or 9599.8%, or 9899.8%.

Embodiment 2: The method of embodiment 1, wherein the N-alkyl nitrophthalimide composition comprises 4-nitro-N—($C_{1-13}$ alkyl)phthalimide, specifically 4-nitro-N-methylphthalimide.

Embodiment 3: The method of embodiment 1 or 2, wherein the N-alkyl nitrophthalimide composition comprises 4-nitro-N—($C_{1-13}$ alkyl)phthalimide and 3-nitro-N—($C_{1-13}$ alkyl)phthalimide, specifically 4-nitro-N-methylphthalimide and 3-nitro-N-methylphthalimide.

Embodiment 4: The method of embodiment 3, wherein the ratio of 4-nitro-N—($C_{1-13}$ alkyl)phthalimide to 3-nitro-N—($C_{1-13}$ alkyl)phthalimide is 0.001:99.999 to 99.999:0.001, preferably 0.01:99.99 to 99.99:0.01, or 1:99 to 99:1, or 90:10 to 99.99:0.01.

Embodiment 5: The method of any one or more of embodiments 1 to 4, further comprising preparing the N-alkyl nitrophthalimide composition by contacting an N—($C_{1-13}$ alkyl)phthalimide with nitric acid and sulfuric acid to provide a nitration product mixture comprising the 4-nitro-N—($C_{1-13}$ alkyl)phthalimide, 3-nitro-N—($C_{1-13}$ alkyl)phthalimide, and 4-hydroxy-3,5-dinitro-N—($C_{1-13}$ alkyl)phthalimide.

Embodiment 6: The method of any one or more of embodiments 1 to 5, wherein the dialkali metal salt of a dihydroxy aromatic compound is of formula (I); the N-alkyl nitrophthalimide composition comprises a compound of formula (III); and the aromatic bisimide is of formula (IV), wherein in the foregoing formulas, M is an alkali metal ion; Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing, and $R^1$ is a monovalent $C_{1-13}$ organic group.

Embodiment 7: The method of embodiment 6, wherein M is sodium.

Embodiment 8: The method of embodiment 6 or 7 wherein Z is a divalent group of formula (IIa) wherein Q is —O—, —S—, —C(O)—, —SO$_2$—, —SO—, or —C$_y$H$_{2y}$— wherein y is an integer from 1-5 or a halogenated derivative thereof, preferably wherein Z is 2,2-(4-phenylene)isopropylidene.

Embodiment 9: The method of any one or more of embodiments 1-8 wherein the aromatic bisimide comprises 4,4'-bisphenol-A-bis-N-methylphthalimide, 3,4'-bisphenol-A-bis-N-methylphthalimide, 3,3'-bisphenol-A-bis-N-methylphthalimide, or a combination comprising at least one of the foregoing.

Embodiment 10: The method of any one or more of embodiments 1-9, wherein the product mixture further comprises a nonpolar organic solvent, preferably wherein the nonpolar organic solvent is toluene.

Embodiment 11: The method of any one or more of embodiments 1-9, wherein the product mixture further comprises a dipolar aprotic solvent, preferably wherein the dipolar aprotic solvent comprises dimethyl sulfoxide, dimethylacetamide, N-methylpyrrolidone, dimethylformamide, sulfolane, or a combination comprising at least one of the foregoing.

Embodiment 12: The method of any one or more of embodiments 1-11, wherein the reacting is in the presence of a phase transfer catalyst, preferably wherein the phase transfer catalyst is hexaethylguanidinium chloride.

Embodiment 13: The method of embodiment 12, wherein the phase transfer catalyst is present in an amount of 0.1-10 mole percent, preferably 1-2 mole percent, based on the total moles of the dialkali metal salt of a dihydroxy aromatic compound.

Embodiment 14: The method of any one or more of embodiments 1-13, wherein the method further comprises extracting the aromatic bisimide from the product mixture-provide an isolated aromatic bisimide, wherein the extracting is with an aqueous alkali solution comprising 0.1-10 wt %, or 1-5 wt % by weight alkali metal hydroxide, preferably sodium hydroxide.

Embodiment 15: The method of embodiment 14, wherein the isolated aromatic bisimide has a YI of less than 25, or less than 10, or less than 5, as determined according to ASTM D-1925.

Embodiment 16: A method for the manufacture of a polyetherimide, the method comprising, contacting an aromatic bisimide prepared by the method of any one or more of embodiments 1-15 with a phthalic anhydride in the presence of a catalyst and under conditions effective to provide an aromatic bis(ether phthalic anhydride) of formula (V) wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of the formula $H_2N$—R—$NH_2$ wherein R is a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof, or a combination comprising at least one of the foregoing; and wherein the polyetherimide has a YI of less than 120, or less than 110, or less than 100, as determined according to ASTM D1925 at a thickness of 3.2 millimeters.

Embodiment 17: A method for the manufacture of a polyetherimide, the method comprising, hydrolyzing an aromatic bisimide prepared by the method of any one or more of embodiments 1-15 under conditions effective to provide the corresponding tetraacid; condensing the tetraacid under conditions effective to provide an aromatic bis(ether phthalic anhydride) of formula (V) wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of formula $H_2N$—R—$NH_2$ wherein R is a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or a halogenated derivative thereof, or a combination comprising at least one of the foregoing; and wherein the polyetherimide has a YI of less than 120, or less than 110, or less than 100, as determined according to ASTM D1925 at a thickness of 3.2 millimeters.

Embodiment 18: A polyetherimide prepared according to the method of embodiments 16 or 17.

Embodiment 19: An article comprising the polyetherimide of embodiment 18, wherein the article is in the form of a fiber, a film, a sheet, a foam, a filament, a molded article, an extruded article, or a powder.

Embodiment 20: A mixed acid nitration process for the preparation of an N-alkyl nitrophthalimide composition, the process comprising contacting an N-alkylphthalimide with nitric acid and sulfuric acid, to provide a dissolved N-alkyl nitrophthalimide product mixture comprising 4-nitro-N—($C_{1-13}$ alkyl)phthalimide, 3-nitro-N—($C_{1-13}$ alkyl)phthalimide, or a combination comprising at least one of the foregoing, and 4-hydroxy-3,5-dinitro-N—($C_{1-13}$ alkyl)phthalimide; adding water to precipitate the N-alkyl nitrophthalimide product mixture, and isolating the precipitated N-alkyl nitrophthalimide product mixture; washing the isolated N-alkyl nitrophthalimide product mixture, preferably wherein the washing is using a belt filter, an agitated nutsche filter, centrifuging, or a combination comprising at least one of the foregoing, to provide a washed N-alkyl nitrophthalimide composition; and optionally purifying the washed N-alkyl nitrophthalimide product mixture by: contacting the washed N-alkyl nitrophthalimide product mixture with an aqueous alkali metal carbonate solution, an aqueous alkali metal hydrogen carbonate solution, or a combination comprising at least one of the foregoing, followed by extracting the 4-nitro-N—($C_{1-13}$ alkyl)phthalimide into an organic solvent provide an aqueous phase and an organic phase; and separating aqueous phase and the organic phase to provide a purified N-alkyl nitrophthalimide composition in the organic phase; or dissolving the washed N-alkyl nitrophthalimide product mixture in an organic solvent immiscible with water to extract the 4-nitro-N—($C_{1-13}$ alkyl)phthalimide into the organic solvent and provide an aqueous phase and an organic phase; adding an aqueous alkali metal carbonate, an aqueous alkali metal hydrogen carbonate, or a combination thereof to the aqueous phase; and separating aqueous phase and the organic phase to provide a purified N-alkyl nitrophthalimide composition in the organic phase; or dissolving the washed N-alkyl nitrophthalimide product mixture in an organic solvent immiscible with water to extract the 4-nitro-N—($C_{1-13}$ alkyl)phthalimide into the organic solvent and provide an aqueous phase and an organic phase; and separating aqueous phase and the organic phase to provide a purified N-alkyl nitrophthalimide composition in the organic phase; and optionally further contacting the organic phase with an aqueous alkali metal hydrogen carbonate solution, or a combination comprising at least one of the foregoing to provide an organic phase comprising a purified N-alkyl nitrophthalimide composition wherein the washed or the purified N-alkyl nitrophthalimide composition comprises 4-nitro-N—($C_{1-13}$ alkyl)phthalimide, 1-10000 ppm, or 1-8000 ppm, or 1-7000 ppm, or 1-6000 ppm, or 1-5000 ppm, or 1-4000 ppm, or 1-3000 ppm, or 500-7000 ppm, 500-6000 ppm, or 500-5000 ppm, or 500-4000 ppm, or 500-3000 ppm, or 1000-7000 ppm or 1000-6000 ppm, or 1000-5000 ppm or 1000-4000 ppm, or 1000-3000 of 4-hydroxy-3,5-dinitro-N—($C_{1-13}$ alkyl)phthalimide, and 0.001-5 wt %, or 0.1 to 3.5 wt. %, or 1-2 wt % of 3-nitro-N—($C_{1-13}$ alkyl)phthalimide.

In general, the compositions, methods, and articles can alternatively comprise, consist of, or consist essentially of, any appropriate components herein disclosed. The compositions, methods and articles can additionally, or alternatively, be formulated so as to be devoid, or substantially free, of any components, materials, ingredients, adjuvants, steps, or species used in the prior art compositions or methods that are otherwise not necessary to the achievement of the function and/or objectives of the present invention.

All ranges disclosed herein are inclusive of the endpoints, and the endpoints are independently combinable with each other. "Combination" is inclusive of blends, mixtures, alloys, reaction products, and the like. "Or" means "and/or." The terms "a" and "an" and "the" do not denote a limitation of quantity, and are to be construed to cover both the singular and the plural, unless otherwise indicated herein or clearly contradicted by context.

As used herein, the term "hydrocarbyl" includes groups containing carbon, hydrogen, and optionally one or more heteroatoms (e.g., 1, 2, 3, or 4 atoms such as halogen, O, N, S, P, or Si). "Alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—$CH_2$—) or propylene (—$(CH_2)_3$—)). "Alkenyl" and "alkenylene" mean a monovalent or divalent, respectively, straight or branched chain hydrocarbon group having at least one carbon-carbon double bond (e.g., ethenyl (—HC=$CH_2$) or propenylene (—HC($CH_3$)=$CH_2$—). "Alkynyl" means a straight or branched chain, monovalent hydrocarbon group having at least one carbon-carbon triple bond (e.g., ethynyl). "Alkoxy" means an alkyl group linked via an oxygen (i.e., alkyl-O—), for example methoxy, ethoxy, and sec-butyloxy. "Cycloalkyl" and "cycloalkylene" mean a monovalent and divalent cyclic hydrocarbon group, respectively, of formula —$C_nH_{2n-x}$— and —$C_nH_{2n-2x}$— wherein x is the number of cyclizations. "Aryl" means a monovalent, monocyclic or polycyclic aromatic group (e.g., phenyl or naphthyl). "Arylene" means a divalent, monocyclic or polycyclic aromatic group (e.g., phenylene or naphthylene). The prefix "halo" means a group or compound including one more halogen (F, Cl, Br, or I) substituents, which can be the same or different. The prefix "hetero" means a group or compound that includes at least one ring member that is a heteroatom (e.g., 1, 2, or 3 heteroatoms, wherein each heteroatom is independently N, O, S, or P.

"Substituted" means that the compound or group is substituted with at least one (e.g., 1, 2, 3, or 4) substituents instead of hydrogen, where each substituent is independently nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ is cycloalkenyl, $C_{6-12}$ aryl, $C_{7-13}$ arylalkylene (e.g., benzyl), $C_{7-12}$ alkylarylene (e.g., toluyl), $C_{4-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)$_2$-aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:

1. A method for producing an aromatic bisimide, the method comprising
reacting a dialkali metal salt of a dihydroxy aromatic compound with an N-alkyl nitrophthalimide composition in the presence of 0.5 to 2 mole percent of a phase transfer catalyst based on the total moles of the dialkali metal salt of the dihydroxy aromatic compound under conditions effective to form a product mixture comprising the aromatic bisimide,
wherein the N-alkyl nitrophthalimide composition is prepared by contacting an N—($C_{1-13}$ alkyl)phthalimide with nitric acid and sulfuric acid to provide a nitration product mixture comprising
4-nitro-N—($C_{1-13}$ alkyl)phthalimide, 3-nitro-N—($C_{1-13}$ alkyl)phthalimide, or a combination comprising at least one of the foregoing; and
4-hydroxy-3,5-dinitro-N—($C_{1-13}$ alkyl)phthalimide in an amount of 500-6400 ppm; and
wherein the phase transfer catalyst is a hexa($C_{1-12}$ alkyl) guanidinium salt, a tetra($C_{1-12}$ alkyl)ammonium salt, or a bis-quaternary salt of the formula $(R^4)_3Q^+(R^3)^+Q(R^4)_3$ $(Br)_2$, wherein each $R^4$ is a $C_{1-4}$ n-alkyl group and $R^3$ is a divalent $C_{1-18}$ alkylene group,
wherein the aromatic bisimide is obtained in a yield of greater than 75%.

2. The method of claim 1, wherein the N-alkyl nitrophthalimide composition comprises 4-nitro-N—($C_{1-13}$ alkyl) phthalimide.

3. The method of claim 1, wherein the N-alkyl nitrophthalimide composition comprises 4-nitro-N—($C_{1-13}$ alkyl) phthalimide and 3-nitro-N—($C_{1-13}$ alkyl)phthalimide, wherein the ratio of 4-nitro-N—($C_{1-13}$ alkyl)phthalimide to 3-nitro-N—($C_{1-13}$ alkyl)phthalimide is 0.001:99.999 to 99.999:0.001.

4. The method of claim 1, wherein
the dialkali metal salt of a dihydroxy aromatic compound is of the formula

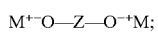

the N-alkyl nitrophthalimide composition comprises a compound of the formula

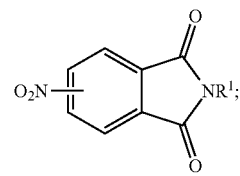

and
the aromatic bisimide is of the formula

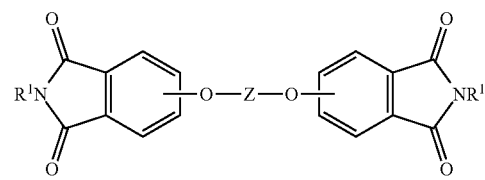

wherein in the foregoing formulas,

M is an alkali metal;

Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and $R^1$ is a monovalent $C_{1-13}$ organic group.

5. The method of claim 4, wherein M is sodium.

6. The method of claim 4, wherein Z is a divalent group of the formula

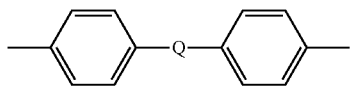

wherein Q is —O—, —S—, —C(O)—, —SO$_2$—, —SO—, or —C$_y$H$_{2y}$— wherein y is an integer from 1-5 or a halogenated derivative thereof.

7. The method of claim 1 wherein the aromatic bisimide comprises 4,4'-bisphenol-A-bis-N-methylphthalimide, 3,4'-bisphenol-A-bis-N-methylphthalimide, 3,3'-bisphenol-A-bis-N-methylphthalimide, or a combination comprising at least one of the foregoing.

8. The method of claim 1, wherein the product mixture further comprises a nonpolar organic solvent.

9. The method of claim 1, wherein the product mixture further comprises a dipolar aprotic solvent.

10. The method of claim 1, wherein the method further comprises extracting the aromatic bisimide from the product mixture to provide an isolated aromatic bisimide, wherein the extracting is with an aqueous alkali solution comprising 0.1-10 wt % by weight alkali metal hydroxide.

11. The method of claim 10, wherein the isolated aromatic bisimide has a yellowness index of less than 75, as determined according to ASTM D-1925.

12. A method for the manufacture of a polyetherimide, the method comprising preparing an aromatic bisimide according to the method of claim 1;

contacting the aromatic bisimide with a phthalic anhydride in the presence of a catalyst and under conditions effective to provide an aromatic bis(ether phthalic anhydride) of the formula

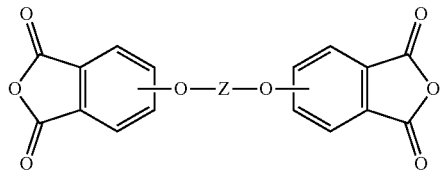

wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of the formula

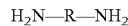

wherein R is a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof, or a combination comprising at least one of the foregoing; and wherein the polyetherimide has a yellowness index of less than 120, as determined according to ASTM D1925 at a thickness of 3.2 millimeters.

13. A method for the manufacture of a polyetherimide, the method comprising, preparing an aromatic bisimide according to the method of claim 1;

hydrolyzing the aromatic bisimide under conditions effective to provide the corresponding tetraacid;

condensing the tetraacid under conditions effective to provide an aromatic bis(ether phthalic anhydride) of the formula

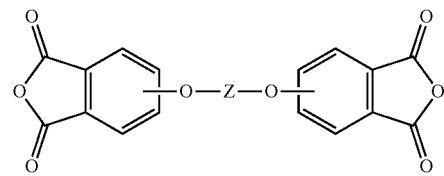

wherein Z is an aromatic $C_{6-24}$ monocyclic or polycyclic moiety optionally substituted with 1-6 $C_{1-8}$ alkyl groups, 1-8 halogen atoms, or a combination comprising at least one of the foregoing; and contacting the aromatic bis(ether phthalic anhydride) with an organic diamine of the formula

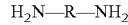

wherein R is a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof, or a combination comprising at least one of the foregoing; and wherein the polyetherimide has a yellowness index of less than 120, as determined according to ASTM D1925 at a thickness of 3.2 millimeters.

* * * * *